United States Patent
Gupta et al.

(10) Patent No.: US 7,300,792 B2
(45) Date of Patent: Nov. 27, 2007

(54) LUX EXPRESSION IN EUKARYOTIC CELLS

(75) Inventors: Rakesh K. Gupta, New Delhi (IN);
Stacy S. Patterson, Knoxville, TN (US); Gary S. Sayler, Blaine, TN (US);
Steven A. Ripp, Knoxville, TN (US)

(73) Assignee: University of Tennessee Research Foundation, Knoxville, TN (US)

( * ) Notice: Subject to any disclaimer, the term of this patent is extended or adjusted under 35 U.S.C. 154(b) by 154 days.

(21) Appl. No.: 10/408,003

(22) Filed: Apr. 4, 2003

(65) Prior Publication Data

US 2004/0002148 A1    Jan. 1, 2004

Related U.S. Application Data

(60) Provisional application No. 60/370,055, filed on Apr. 4, 2002.

(51) Int. Cl.
*C12N 15/85* (2006.01)
*C12N 1/19* (2006.01)

(52) U.S. Cl. ..................... 435/325; 435/254.2

(58) Field of Classification Search ........... 435/254.11, 435/254.21, 254.22, 254.23, 254.3, 325
See application file for complete search history.

(56) References Cited

U.S. PATENT DOCUMENTS 5,571,722 A * 11/1996 Rosson ..................... 435/320.1
5,834,237 A * 11/1998 Jacobs et al. ............... 435/69.1
2003/0096322 A1* 5/2003 Giuliano et al. ............ 435/7.21

OTHER PUBLICATIONS

Liger et al., J. Biol. Chem., vol. 279, No. 33, pp. 34890-34897, 2004.*
Zhou et al., Proc. Natl. Acad. Sci. USA, vol. 98, No. 4, pp. 1531-1536, 2001.*
Daunert et al., "Genetically Engineered Whole-Cell Sensing Systems: Coupling Biological Recognition with Reporter Genes," Chem. Rev., 100: 2705-2738, 2000.
D'Souza, S., "Microbial biosensors," Biosensors & Bioelectronics, 16: 337-353, 2001.
Kohler et al., "Reporter gene bioassays in environmental analysis," Fresenius J. Anal Chem, 366: 767-779, 2000.
Routledge, E. and J. Sumpter, "Estrogenic Activity of Surfactants and Some of Their Degradation Products Assessed Using a Recombinant Yeast Screen," Environmental Toxicology and Chemistry, 15: 241-248, 1996.
Almashanu et al., "Fusion of LuxA and LuxB and its Expression in *E. coli, S. cerevisiae* and *D. Melanogaster*," J. Biolumin. Chemilumin., 5: 89-97, 1990.
Boylan et al., "Fused Bacterial Luciferase Subunits Catalyze Light Emission in Eukaryotes and Prokaryotes," 264: 1915-1918, 1989
Kirchner et al.,"Active bacterial luciferase from a fused gene: expression of a *Vibrio harveyi* luxAB translational fusion in bacteria, yeast and plant cells," Gene, 81: 349-354, 1989.
Olsson et al., "Engineering of monomeric bacterial luciferase by fusion of luxA and luxB genes in *Vibrio harveyi*," 81: 335-347, 1989.
Hellen, C. and P. Sarnow, "Internal ribosome entry sites in eukaryotic mRNA molecules," Genes & Development, 15: 1593-1612, 2001.
Baker, V., "Endocrine disrupters—testing strategies to assess human hazard," Toxicology in Vitro, 15: 413-419, 2001.
Hollis, R.P. et al.: FEBS Lett., vol. 506, 2001, pp. 140-142.
Bessoule, J.J. et al.: FEBS Lett., vol. 214, 1987, pp. 158-162, 1987.
Meighen, E.A. and P.V. Dunlap: Adv. Microb. Physiol., vol. 34, 1993, pp. 1-67.
Johnson, D.R. et al.: J. Biol. Chem., vol. 269, 1994, pp. 18037-18046.
Gan, W.N. and R.E. Rhoads: J. Biol. Chem., vol. 271, 1996, pp. 623-626.
Henstrand, J.M. et al.: Mol. Microbiol., vol. 22, 1996, pp. 859-866.
Gradi, A.H. et al.: Mol. Cell. Biology, vol. 18, 1998, pp. 334-342.
Miller, C.A. et al.: Nuc. Acids Res., vol. 26, 1998, pp. 3577-3583.
Rajala, R.V.S. et al.: Mol. and Cell. Biochem., vol. 204, 2000, pp. 135-155.
Gunaratne, R.S. et al: Biochem. J., vol. 348, pp. 459-463, 2000.
Kozak, M.: Bol. Cell. Biol., vol. 21, 2001, pp. 1899-1907.

* cited by examiner

*Primary Examiner*—Nancy Vogel
(74) *Attorney, Agent, or Firm*—Ruden McClosky; Stanley A. Kim

(57) ABSTRACT

The luxA, B, C, D, and E genes from *Photorhabdus luminescens* have been introduced into *Saccharomyces cerevisiae* bioluminescent yeast cells.

19 Claims, 7 Drawing Sheets

LUX EXPRESSION IN EUKARYOTIC CELLS

CROSS REFERENCE TO RELATED APPLICATION

The present application claims the priority of U.S. provisional patent application No. 60/370,055 filed Apr. 4, 2002.

STATEMENT AS TO FEDERALLY SPONSORED RESEARCH

The invention was made with U.S. government support under grant number 5R21 RR14169 awarded by the National Institutes of Health, and grant number ORNL 98-0520 awarded by the Department of Energy. The U.S. government may have certain rights in the invention.

FIELD OF THE INVENTION

The invention relates generally to the fields of molecular biology, microbiology, and microprocessing. More particularly, the invention relates to expression of bacterial lux genes in eukaryotic cells.

BACKGROUND

Cloning and expression of the luxAB genes and the entire luxCDABE cassette from different luminescent organisms (*Vibrio fischeri*, *V. harveyi*, and *Photorhabdus luminescens*) has led to the widespread and expanding application of the bacterial lux system as a reporter of gene expression and regulation (Liu, et al., Plasmid, 44:250-261, 2000), as well as a sensor of environmental pollutants and metabolic functions in a wide range of prokaryotic organisms (Applegate et al., Appl. Environ. Microbiol., 64:2730-2735, 1998 and Sayler, G. S., and Ripp, S., Current Opinion in Biotechnology, 11:286-289, 2000).

Bacterial luciferase expressed from luxAB genes catalyzes the oxidation of reduced riboflavin 5'-phosphate ($FMNH_2$) and a long-chain aliphatic aldehyde (tetradecanal) synthesized by luxCDE genes, yielding FMN (flavin mononucleotide), fatty acid, water, and greenish blue light. The cofactor, FMNH2, is provided by the flavin oxidoreductase enzyme (NADPH-FMN Oxidoreductase or FMN oxidoreductase) in prokaryotes. Engineering schemes using only the luxAB genes require the addition of exogenous aldehyde substrate, typically n-decylaldehyde, to generate a bioluminescent response. Use of the entire luxCDABE operon, however, allows for intrinsic whole-cell bioluminescence without the requirement for exogenous addition of chemicals or co-factors. Thus, the bioreporter remains completely self-sufficient in its ability to produce visible light in response to specific chemicals or physical agents. Consequently, the luxCDABE system has found unusual applications as remote, real-time, reagentless components in bioelectronic devices, whole cell logic gates for biocomputing, in situ functional imaging and analysis of recombinant strain released to the environment and in vivo imaging of the course of systemic infection in animal hosts While both luxAB and luc (firefly luciferase) have been used as reporters of gene expression in eukaryotic cells; a reagentless real-time bioreporter system independent of an exogenous substrate or an excitation source such as needed for GFP, has not been available for eukaryotic applications in research, medicine or biotechnology. In contrast to gene expression in bacterial hosts where the lux cassette is transcribed as a polycistronic mRNA, eukaryotic systems generally require a separate promoter preceding each gene. This stringent requirement of gene expression has limited the application of bacterial lux genes in eukaryotic organisms solely to luxAB derivatives. Fused luxAB genes have been constructed, allowing for the expression of luciferase under a single promoter in eukaryotic hosts including *Saccharomyces cerevisiae*, mammalian, plant, and insect cells, as well as in vitro in reticulocyte lysates. In these fusions, the carboxyl terminal of the α subunit of the luciferase is linked by a short polypeptide ranging from 1-22 amino acids to the amino terminal of the β subunit by eliminating the stop codons of the α subunit. Although luxAB fusions can generate bioluminescence when supplemented with a requisite aldehyde substrate, relative levels of activity vary widely depending on the expression system, growth assay, and availability of the cofactor, $FMNH_2$. For example, luminescence levels not more than 2000 times above background were detected during constitutive expression of a fused luxAB construct under the control of a PGK promoter in *S. cerevisiae*.

In addition to luxAB fusions, attempts have also been made to simultaneously express luxA and luxB separately from a dual promoter expression system. Successful expression and assembly of the *V. harveyi* luciferase protein subunits into a functional dimeric form has been demonstrated in plant protoplasts, transformed calli, and leaves of transformed plants (Koncz et al., Proceedings of the National Academy of Sciences of the United States of America, 84:131-135, 1987). Although the independently expressed subunits remain stable, protein folding kinetics upon fusion are significantly altered as a function of temperature, which proves especially detrimental in eukaryotic systems (Escher et al., Molecular and Cellular Biology, 13:4860-4874, 1989). Moreover, generation of in vivo bioluminescence in eukaryotic cells is difficult because the availability of the cofactor, $FMNH_2$, is limited for the bioluminescent reaction (Meighen, E. A., Microbiological Reviews, 55:123-142, 1991). Therefore, direct measurement of bacterial luciferase activity in eukaryotes without disruption of the cell membrane and loss of cell viability has yet to be achieved.

The use of the prokaryotic lux-based bioluminescent reporter system for transcriptional fusions has revolutionized both applied and basic research capabilities by allowing for real-time, reagentless monitoring of a wide variety of extracellular analytes and intracellular genetic events. However, the same technology has not been available for eukaryotic applications. Although both GFP and Luc reporter proteins are commonly used in eukaryotic systems, both are subject to external manipulations (exogenous light excitations or luciferin additions) prior to quantitation and cannot be exploited in reagentless, real-time, on-line bioassays.

Reporter proteins including bacterial luciferase (LuxAB), β-galactosidase, chloramphenicol acetyltransferase (CAT), green fluorescent protein (GFP) and firefly luciferase (Luc) have been widely used as indicators of gene expression and regulation as well as sensors of metabolic functions in both prokaryotic and eukaryotic systems (Greer and Szalay Luminescence 17:43-74, 2002). However, the requirement of an exogenous substrate or excitation source in these reporter assays has restricted their use primarily to laboratory and in vitro applications. Accordingly, there exists a need for a self-sustaining bioluminescent system in eukaryotic cells.

SUMMARY

The invention relates to the first functional expression of a complete, prokaryotic luxCDABE gene cassette from *Photorhabdus luminescens* in the yeast *Saccharomyces cerevisiae* to generate a fully autonomous bioluminescent eukaryotic bioreporter. Bioluminescence levels from this engineered yeast strain are maintained by co-expression of the *Vibrio harveyi* flavin-reductase gene (frp) responsible for providing the enzyme co-factor, $FMNH_2$, required for the bioluminescent reaction. With bioluminescence approaching more than $10^7$ photons/sec, this bioreporter technology will prove useful in a wide variety of applications including remote sensing, high-throughput drug and chemical screening, biocomputing, in situ functional imaging and analysis, and non-invasive in vivo imaging of disease progression.

Accordingly, the invention features a eukaryotic cell including LuxA, LuxB, LuxC, LuxD, and LuxE. In one variation, the cell further includes FMN oxidoreductase. The eukaryotic cell can also include a nucleic acid encoding LuxA, a nucleic acid encoding LuxB, a nucleic acid encoding LuxC, a nucleic acid encoding LuxD, and a nucleic acid encoding LuxE. In some embodiments, the cell also includes a nucleic acid encoding FMN oxidoreductase. The nucleic acids can be capable of being expressed in the eukaryotic cell.

In cells including a nucleic acid encoding LuxA, LuxB, LuxC, LuxD, LuxE, or FMN oxidoreductase, the nucleic acid can be operatively linked to at least one regulatory element, e.g., one responsive to an analyte. In some variations, the regulatory element includes or is operatively linked to a promoter sequence. e.g., a constitutive or inducible promoter. The regulatory element can include an IRES, e.g., eukaryotic IRES such as a yeast (e.g., *Saccharomyces cerevisiae*) IRES.

The eukaryotic cell of the invention can be a yeast cell such as a *Saccharomyces cerevisiae* cell or a *Candida albicans* cell. The eukaryotic cell can be luminescent. For certain applications, the cell is contained on or within a solid substrate (e.g., a microchip).

Unless otherwise defined, all technical terms used herein have the same meaning as commonly understood by one of ordinary skill in the art to which this invention belongs.

As used herein, a "nucleic acid" or a "nucleic acid molecule" means a chain of two or more nucleotides such as RNA (ribonucleic acid) and DNA (deoxyribonucleic acid). A "purified" nucleic acid molecule is one that has been substantially separated or isolated away from other nucleic acid sequences in a cell or organism in which the nucleic acid naturally occurs (e.g., 30, 40, 50, 60, 70, 80, 90, 95, 96, 97, 98, 99, 100% free of contaminants). The term includes, e.g., a recombinant nucleic acid molecule incorporated into a vector, a plasmid, a virus, or a genome of a prokaryote or eukaryote. Examples of purified nucleic acids include cDNAs, fragments of genomic nucleic acids, nucleic acids produced by polymerase chain reaction (PCR), nucleic acids formed by restriction enzyme treatment of genomic nucleic acids, recombinant nucleic acids, and chemically synthesized nucleic acid molecules. A "recombinant" nucleic acid molecule is one made by an artificial combination of two otherwise separated segments of sequence, e.g., by chemical synthesis or by the manipulation of isolated segments of nucleic acids by genetic engineering techniques.

As used herein, "protein" or "polypeptide" are used synonymously to mean any peptide-linked chain of amino acids, regardless of length or post-translational modification, e.g., glycosylation or phosphorylation. A "purified" polypeptide is one that has been substantially separated or isolated away from other polypeptides in a cell or organism in which the polypeptide naturally occurs (e.g., 30, 40, 50, 60, 70, 80, 90, 95, 96, 97, 98, 99, 100% free of contaminants).

As used herein, the term "vector" refers to a nucleic acid molecule capable of transporting another nucleic acid to which it has been linked. One type of preferred vector is an episome, i.e., a nucleic acid capable of extra-chromosomal replication. Another type of preferred vector is one that integrates within the host cell genome. Preferred vectors are those capable of autonomous replication and/expression of nucleic acids to which they are linked. Vectors capable of directing the expression of genes to which they are operatively linked are referred to herein as "expression vectors."

A first nucleic-acid sequence is "operably" linked with a second nucleic-acid sequence when the first nucleic-acid sequence is placed in a functional relationship with the second nucleic-acid sequence. For instance, a promoter is operably linked to a coding sequence if the promoter affects the transcription or expression of the coding sequence. Generally, operably linked nucleic acid sequences are contiguous and, where necessary to join two protein coding regions, in reading frame.

A cell, tissue, or organism into which has been introduced a foreign nucleic acid, such as a recombinant vector, is considered "transformed," "transfected," or "transgenic. "A "transgenic" or "transformed" cell or organism (e.g., a yeast) also includes progeny of the cell or organism, including progeny produced from a breeding program employing such a "transgenic" cell or organism as a parent in a cross. For example, a yeast cell transgenic for luxA, luxB, luxC, luxD, or luxE is one in which a luxA, luxB, luxC, luxD, or luxE nucleic acid has been introduced. Similarly, a yeast cell transgenic for luxA, luxB, luxC, luxD, and luxE is one in which luxA, luxB, luxC, luxD, and luxE nucleic acids have been introduced.

Although methods and materials similar or equivalent to those described herein can be used in the practice or testing of the present invention, suitable methods and materials are described below. All publications, patent applications, patents and other references mentioned herein are incorporated by reference in their entirety. The particular embodiments discussed below are illustrative only and not intended to be limiting.

BRIEF DESCRIPTION OF THE DRAWINGS

The above and further advantages of this invention may be better understood by referring to the following description taken in conjunction with the accompanying drawings, in which.

DETAILED DESCRIPTION

Figure 1:
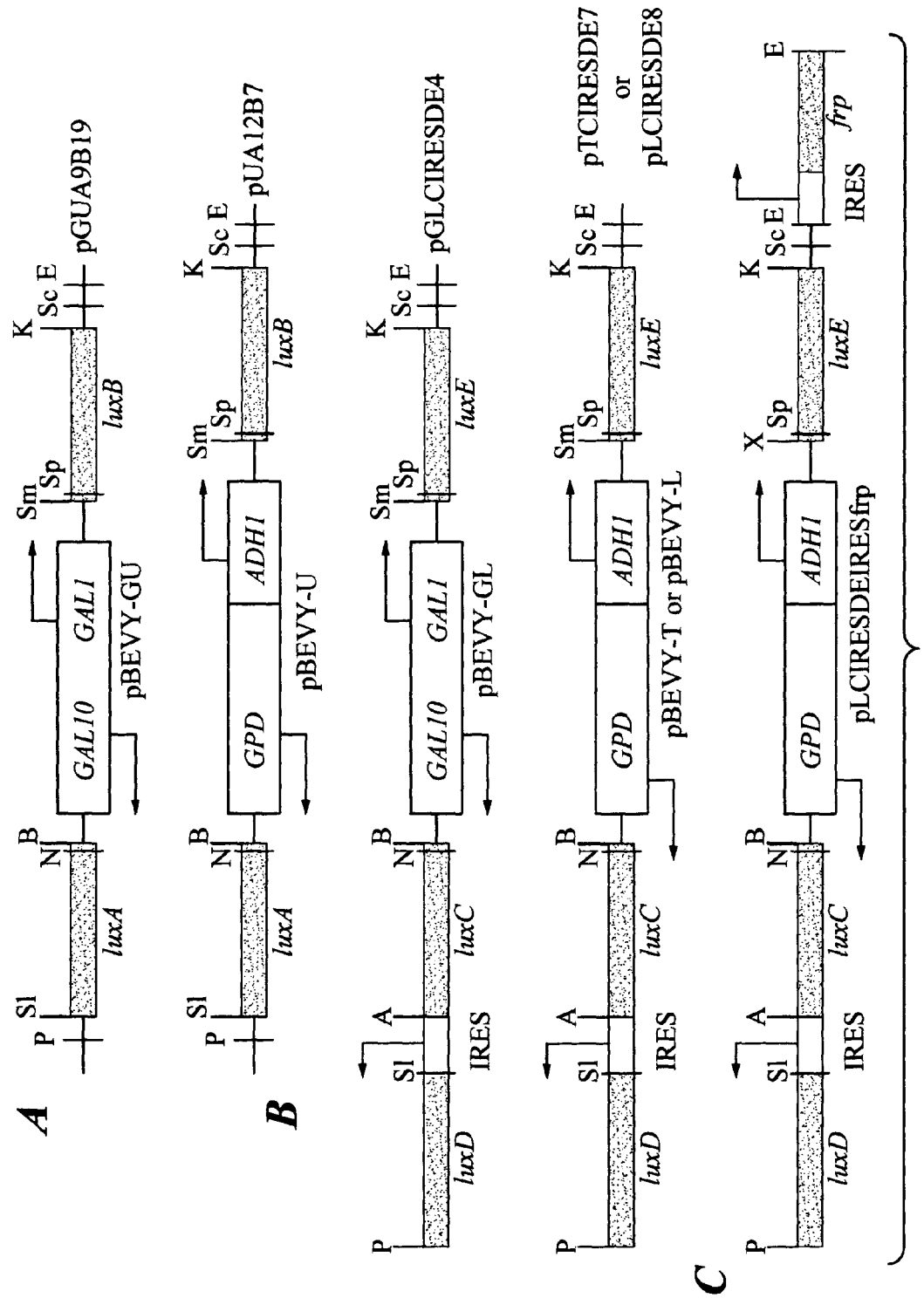
FIG. 1. is a schematic representation of constructs used for expression of the luxCDABE genes from *P. luminescens* in *S. cerevisiae* (not to scale).

A bacterial lux-based yeast bioreporter capable of emitting light without exogenous substrate addition has been constructed. The luxA, B, C, D, and E genes from P. luminescens were cloned and expressed in S. cerevisiae. Functional expression of these bacterial genes in S. cerevisiae was examined. To construct bioluminescent yeast cells, a bi-directional pBEVY series of vectors, both constitutive and inducible, were used as cloning and expression tools. The luxA and luxB genes were cloned bi-directionally in the pBEVY-U and pBEVY-GU vectors while the luxC and luxE genes were expressed bi-directionally in the pBEVY-T, pBEVY-GL and pBEVY-L vectors. The luxD gene, encoding an acyl-ACP transferase, was fused to a yeast internal ribosomal entry site (IRES) sequence to achieve high expression. The bioluminescence from these yeast cells was stabilized by co-expressing the frp gene from V. harveyi. The elevated levels of luminescence exhibited by the lux-bearing S. cerevisiae cells in the absence of exogenous aldehyde indicate that these cells can be used as potential reporters of gene regulation and expression as well as for on-line, real-time detection of environmental pollutants.

The constructs containing luxA and luxB genes when transformed into S. cerevisiae (ura⁻trp⁻leu⁻) auxotrophs generated ~5.0 million photon counts/sec/OD (42000 times background) on addition of aldehyde (1% decanal). Addition of aldehyde to the cells containing the recombinant luxAB genes is not required for light emission if the luxCDE genes responsible for aldehyde synthesis are also expressed. The luxC and luxE genes were cloned into other bi-directional vectors (pBEVY-T, pBEVY-L) consisting of the same promoters but different selection markers. The last gene, luxD, responsible for a transferase was cloned downstream of luxE fused to a yeast IRES sequence. Co-transfection of yeast cells with two constructs pBEVY-U luxAB genes and pBEVY-L/luxCDE genes produced recombinants generating light independently without addition of aldehyde. However, when luxA, B, C, D, and E genes were expressed simultaneously, a maximum bioluminescence of $2.8 \times 10^6$ photons/sec/OD was recorded in the strain W303a, without aldehyde addition, during the late logarithmic growth phase. The luminescence from these samples started decaying immediately after a high intensity peak and reached a base line of $2.5 \times 10^5$ photons/sec/OD within 20 sec.

To overcome this instability in continuous bioluminescence production, a flavin oxidoreductase gene (frp) from Vibrio harveyi was co-expressed to provide sufficient concentrations of the co-factor, FMNH2, for the luminescent reaction. The co-expression of frp gene along with luxA, B, C, D and E in yeast not only stabilized but also enhanced the bioluminescence tremendously to $9.0 \times 10^6$ photons/sec/OD. The construction of this lux based yeast bioreporter, which is completely self-sufficient in its ability to produce visible light will allow development of eukaryotic bioreporter and sensing technology.

Additionally, luxCDABE genes were inserted and expressed in the hER strain of S. cerevisiae which contains a chromosomally-based human estrogen response element to produce a lux-based bioreporter (strain BLYES) for environmental endocrine disruptors. The functionality of this strain was compared to that of a traditional lacZ-based yeast estrogen screen (YES) (Routledge et al., Environ. Toxicol. Chem. 15:241-248, 1996). Whereas the lacZ system requires an optimal incubation period from 2-4 days, the luxCDABE system generated a self-directed bioluminescent response within 2-4 h of estrogen exposure with no user intervention, although at 5 to 10-fold lower potency. In an on-line, microchip flow-cell (Bolton et al., Sens. Actuators B 85:179-185, 2002), strain BLYES was able to remotely sense environmentally relevant concentrations of 17β-estradiol in wastewater effluent within 5 h.

The below described preferred embodiments illustrate various compositions and methods within the invention. Nonetheless, from the description of these embodiments, other aspects of the invention can be made and/or practiced based on the description provided below.

Biological Methods

Methods involving conventional molecular biology techniques are described herein. Such techniques are generally known in the art and are described in detail in methodology treatises such as Molecular Cloning: A Laboratory Manual, 3rd ed., vol. 1-3, ed. Sambrook et al., Cold Spring Harbor Laboratory Press, Cold Spring Harbor, N.Y., 2001; and Current Protocols in Molecular Biology, ed. Ausubel et al., Greene Publishing and Wiley-Interscience, New York, 1992 (with periodic updates). Methods for chemical synthesis of nucleic acids are discussed, for example, in Beaucage and Carruthers, Tetra. Letts. 22:1859-1862, 1981, and Matteucci et al., J. Am. Chem. Soc. 103:3185, 1981. Chemical synthesis of nucleic acids can be performed, for example, on commercial automated oligonucleotide synthesizers. Methods involving conventional biology and microbiology are also described herein. Such techniques are generally known in the art and are described in detail in methodology treatises such as Sambrook et al., supra; Current Protocols in Molecular Biology, ed. Ausubel et al., Greene Publishing and Wiley-Interscience, New York, 1992 (with periodic updates); Techniques in Microbial Ecology, ed. Robert S. Burlage et al., Oxford University Press, New York, N.Y., 1998; Environmental Microbiology, ed. Raina M. Maier, Academic Press, Burlington, Mass., 2000; and Environmental Molecular Microbiology: Protocols and Applications, ed. Paul. A Rochelle, Bios Scientific Publishing, Ltd., Oxford, UK, 2001. Methods involving culturing and manipulation of yeast cells are described in Methods In Yeast Genetics: A Cold Spring Harbor Laboratory Course Manual, 2002, Cold Spring Harbor Laboratory Press, Cold Spring Harbor, N.Y.

lux Nucleic Acids and Lux Proteins

The invention relates to eukaryotic cells containing LuxA, LuxB, LuxC, LuxD, and LuxE proteins. In the examples described herein, LuxA, LuxB, LuxC, LuxD, and LuxE were derived from wild-type P. luminescens. The amino acid sequences of native P. luminescens LuxA, LuxB, LuxC, LuxD, and LuxE proteins are listed in Genbank as accession numbers AAK98554 (LuxA), AAK98555 (LuxB), AAK98552 (LuxC), AAK98553 (LuxD), and AAK98556 (LuxE). LuxA, LuxB, LuxC, LuxD, and LuxE derived from other strains or organisms might be used so long as they can be expressed in eukaryotes to generate luminescence. For example, LuxA, LuxB, LuxC, LuxD, and LuxE proteins from *Vibrio harveyi, Xenorhabdus luminescens, Photobacterium phosphoreum, Photobacterium leiognathi,* and *Shewanella hanedai* might be used in the invention. In addition, mutant forms of these proteins or non-naturally occurring variant forms of these proteins might be used. Examples of variants of native *P. luminescens* LuxA, LuxB, LuxC, LuxD, and LuxE proteins include fragments, analogs and derivatives of native *P. luminescens* LuxA, LuxB, LuxC, LuxD, and LuxE proteins. Other variants include, e.g., a protein(s) encoded by a naturally occurring allelic variant of native *P. luminescens* LuxA, LuxB, LuxC, LuxD, and LuxE proteins, a polypeptide(s) encoded by a homolog of native *P. luminescens*, and a polypeptide(s) encoded by a non-naturally occurring variant of *P. luminescens* LuxA, LuxB, LuxC, LuxD, and LuxE proteins. Recombinant forms of the LuxA, LuxB, LuxC, LuxD, and LuxE proteins might also be used.

Nucleic acid molecules encoding the foregoing LuxA, LuxB, LuxC, LuxD, and LuxE proteins may also be utilized in the invention. They may be in the form of RNA or in the form of DNA (e.g., cDNA, genomic DNA, and synthetic DNA). The DNA may be double-stranded or single-stranded. As one example, the coding sequences which encode native *P. luminescens* LuxA, LuxB, LuxC, LuxD and LuxE proteins are listed in Genbank as accession numbers AF403784, M62917, M55977, M90092, and M90093. Other nucleic acid molecules within the invention are those that encode fragments, analogs and derivatives of LuxA, LuxB, LuxC, LuxD and LuxE proteins; those that encode LuxA, LuxB, LuxC, LuxD and LuxE from organisms other than native *P. luminescens*; and those that encode mutant forms of these proteins or non-naturally occurring variant forms of these proteins. For example, nucleic acids that have a nucleotide sequence that differs from native luxA, luxB, luxC, luxD and luxE in one or more bases might be used. For instance, the nucleotide sequence of such variants can feature a deletion, addition, or substitution of one or more nucleotides of a native luxA, luxB, luxC, luxD or luxE.

frp Nucleic Acids and NADPH-FMN Oxidoreductase/FMN Oxidoreductase Protein

Eukaryotic cells of the invention can also include NAD(P)H-flavin oxidoreductase protein (FMN Oxidoreductase, also known as NADPH-FMN Oxidoreductase) from luminescent bacteria, in addition to LuxA, LuxB, LuxC, LuxD, and LuxE proteins. NAD(P)H-flavin oxidoreductases (flavin reductases (FR)) are a class of enzymes capable of catalyzing the reduction of flavin by NAD(P)H and producing reduced flavin for bacterial bioluminescence and other biological processes (Lei et al., J. Bacteriol. 176:3552-3558, 1994). Bioluminescence from eukaryotic cells of the invention (e.g., yeast cells) is stabilized by expressing FMN Oxidoreductase in the cells.

In the examples described herein, FMN Oxidoreductase was derived from wild-type *Vibrio harveyi*. The amino acid sequence of native *V. harveyi* FMN Oxidoreductase protein is listed in Genbank as accession number AAA21331. FMN Oxidoreductase derived from other strains or organisms might be used so long as they can be expressed in eukaryotes to generate luminescence. For example, FMN Oxidoreductase proteins from *V. harveyi, V. fischeri, E. coli,* and *Helicobacter pylori* might be used in the invention. In addition, mutant forms of these proteins or non-naturally occurring variant forms of these proteins might be used. Examples of variants of native *V. harveyi* FMN Oxidoreductase protein include fragments, analogs and derivatives of native *V. harveyi* FMN Oxidoreductase protein. Other variants include, e.g., a protein(s) encoded by a naturally occurring allelic variant of native *V. harveyi* FMN Oxidoreductase protein, a polypeptide(s) encoded by a homolog of native *V. harveyi*, and a polypeptide(s) encoded by a non-naturally occurring variant of *V. harveyi* FMN Oxidoreductase protein. Recombinant forms of the FMN Oxidoreductase protein might also be used.

Nucleic acid molecules encoding the foregoing FMN Oxidoreductase proteins may also be utilized in the invention. They may be in the form of RNA or in the form of DNA (e.g., cDNA, genomic DNA, and synthetic DNA). The DNA may be double-stranded or single-stranded. As one example, the coding sequence which encodes native *V. harveyi* FMN Oxidoreductase protein is listed in Genbank as accession number U08996. Other nucleic acid molecules within the invention are those that encode fragments, analogs and derivatives of FMN Oxidoreductase protein; those that encode FMN Oxidoreductase protein from organisms other than native *V. harveyi*; and those that encode mutant forms of these proteins or non-naturally occurring variant forms of these proteins. For example, nucleic acids that have a nucleotide sequence that differs from native frp in one or more bases might be used. For instance, the nucleotide sequence of such variants can feature a deletion, addition, or substitution of one or more nucleotides of native frp.

Mixtures of Nucleic Acids

A mixture of nucleic acids for inducing luminescence in a eukaryotic cell is also within the invention. A mixture of nucleic acids for inducing luminescence in a eukaryotic cell includes a nucleic-acid encoding LuxA, a nucleic acid encoding LuxB, a nucleic acid encoding LuxC, a nucleic acid encoding LuxD, and a nucleic acid encoding LuxE. Within this mixture, at least one of the nucleic acids can be operatively linked to a regulatory element that facilitates its expression in a eukaryotic cell. In some applications, the mixture further includes a nucleic acid encoding FMN Oxidoreductase. In preferred embodiments, the nucleic acid encoding FMN Oxidoreductase is frp from *V. harveyi*.

Cells Containing lux Nucleic Acids

Eukaryotic cells suitable for use in the invention include any capable of expressing LuxA, LuxB, LuxC, LuxD, and LuxE. Examples of eukaryotic cells include animal cells, plant cells, algae, fungi, yeast, and protozoa. In the examples described herein, LuxA, LuxB, LuxC, LuxD, LuxE and FMN Oxidoreductase proteins are expressed in *S. cerevisiae*. Yeast other than *S. cerevisiae*, e;g., *Candida* species (e.g., *C. dubliniensis*, *C. norvegensis*, *C. lusitaniae*, *C. tropicalis*, *C. krusei*, *C. glabrata*, *C. inconspicua*), *Aspergillus* species (e.g., *A. fumigatus, A. nidulans, A. parasiticus, A. flavus*), *Histoplasma* species (e.g., *H. capsulatum*), *Schizosacharomyces* species (e.g., *S. pombe*), and *Pichia* species (e.g., *P. pastoris, P. methanolica*) might also be used in the invention.

In one aspect of the invention, LuxA, LuxB, LuxC, LuxD, and LuxE are expressed in mammalian cells. To facilitate expression of LuxA, LuxB, LuxC, LuxD, LuxE and FMN Oxidoreductase proteins in mammalian cells, for example, one or more nucleic acids encoding these proteins may be operatively linked to an IRES element that functions in mammalian cells. Many IRESs capable of functioning in mammalian cells are known and include those of poliovirus (Schlatter and Fussenegger Biotechnol. Bioeng. 81:1-12, 2003), porcine teschovirus-1 (Kaku et al., J. Virol. 76:11721-11728, 2002), encephalomyocarditis virus (Gorski and Jones, NAR 27:2059-2061, 1999; and Gurtu et al., Biochem. Biophys. Res. Commun. 229:295-298, 1996), rhopalosiphum padi virus (Woolaway et al., J. Virol. 75:10244-10249, 2001), Epstein-Barr virus (Isaksson et al., Oncogene 22:572-581, 2003), as well as IRESs from human genes (Wong et al., Gene Ther. 9:337-344, 2002).

Cells of the invention may include nucleic acids encoding LuxA, LuxB, LuxC, LuxD, LuxE and FMN Oxidoreductase proteins as episomes (e.g., plasmids) or as chromosomally-integrated nucleic acids. In some applications, integration of heterologous genes into the chromosome is preferred for long-term stability of gene expression. To integrate nucleic acids encoding LuxA, LuxB, LuxC, LuxD, LuxE and FMN Oxidoreductase proteins into a yeast cell chromosome, a number of methods may be employed. For example, segments of DNA may be integrated into the yeast chromosome in a site-directed manner via homologous recombination (Wang and Reed, Nature 364:121-126, 1993; Ekino et al., Appl. Environ. Microbiol. 68:5693-5697, 2002; and Sakai et al., Appl. Microbiol. Biotechnol. 33:302-306, 1996). In this method, plasmids harboring a nucleic acid to be integrated are linearized and introduced into yeast cells using a suitable transformation method (e.g., lithium acetate method, Schiestl and Gietz, Curr. Genet. 16:339-346, 1989). In addition to homologous recombination, intergrase-mediated insertion of DNA into the chromosome may be used. For example, Ty1 retrotransposon-mediated chromosomal integration may be useful for integrating nucleic acids enocding LuxA, LuxB, LuxC, LuxD, LuxE and FMN Oxidoreductase proteins into a yeast cell chromosome (Lee and Da Silva Biotechnol. Prog. 12:548-554, 1996; and Jacobs et al., Gene 67:259-269, 1988). Methods for inserting nucleic acids into organisms other than yeast (e.g., mammalian) are known in the art. See Ryan and Sigmund Semin, Nephrol, 22:154-160, 2002; Harris et al., Anal. Biochem. 310:15-26, 2002; Osumi and Inoue Methods 24:35-42, 2001; Bode et al., Biol. Chem. 381:801-813, 2002, Sambrook et al., supra; and Wu et al., J. Virology 72:5919-5926, 1998.

Regulatory Elements

One aspect of the invention relates to the use of nucleic acids that encode LuxA, LuxB, LuxC, LuxD, LuxE and FMN Oxidoreductase proteins. In some applications, one or more of the nucleic acids encoding LuxA, LuxB, LuxC, LuxD, LuxE and FMN Oxidoreductase are operably linked to one or more regulatory elements. Operably linked nucleic acid sequences can be contiguous and, where necessary to join two protein coding regions, in reading frame. Operably linked nucleic acid sequences can also be non-contiguous. Examples of regulatory elements include promoters, enhancers, initiation sites, polyadenylation (polyA) tails, IRES elements, response elements, and termination signals.

To achieve appropriate levels of LuxA, LuxB, LuxC, LuxD, LuxE and FMN Oxidoreductase proteins, any of a number of promoters suitable for use in the selected host cell may be employed. For example, constitutive promoters of different strengths can be used to express the LuxA, LuxB, LuxC, LuxD, LuxE and FMN Oxidoreductase proteins. Inducible promoters may also be used in compositions and methods of the invention. To achieve regulated expression of LuxA, LuxB, LuxC, LuxD, LuxE and FMN Oxidoreductase proteins in yeast cells, GPD, ADH1, GAL1 and GAL10 promoters are preferred, however, any yeast promoter may be used. Other promoters for use in the invention include those from organisms other than yeast (e.g., mammalian cells). For example, to achieve regulated expression of LuxA, LuxB, LuxC, LuxD, LuxE and FMN Oxidoreductase proteins in mammalian cells, any promoter known to function in the mammalian cell may be used.

To facilitate expression of a nucleic acid, the nucleic acid may be operatively linked to an IRES element. IRES elements allow ribosomes to bind directly at an AUG start codon rather than requiring initial recognition at the 5' cap site and subsequent scanning for the start site (Hellen and Sarnow, Genes Dev. 15:1593-1612, 2001). If the AUG start site is located within the open reading frame, translation can be initiated internally and a monocistronic mRNA essentially becomes multiply-cistronic. The insertion of an IRES fragment between lux (e.g., luxA, luxB, luxC, luxD, luxE) nucleic acids facilitates bicistronic synthesis of Lux proteins. Similarly, insertion of an IRES fragment between lux (e.g., luxA, luxB, luxC, luxD, luxE) and frp nucleic acids facilitates bicistronic synthesis of Lux and FMN Oxidoreductase proteins. Preferred IRES elements for use in the invention include the IRES fragment within the 5' leader sequence of *S. cerevisiae* p150 mRNAs (Zhou, W. et al., Proc. Natl. Acad. Sci. U.S.A. 98:1531-1536, 2001). Examples of other IRES elements that may be useful in the invention include YAP1 mRNA leader sequences (Zhou, W. et al., Proc. Natl. Acad. Sci. U.S.A. 98:1531-1536, 2001), IGR IRES (Thompson, S. R., et al., Proc. Natl. Acad. Sci. U.S.A. 98:12972-12977, 2001), poliovirus IRES (Coward, P. and Dasgupta, A., Journal of Virology, 66:286-295, 1992), hepatitis C and coxsackievirus B1 IRES (Iizuka, N. et al., Molecular and Cellular Biology, 14:7322-7330, 1994), and the *E. coli* lacI segment (Paz et al., Journal of Biological Chemistry, 274:21741-21745, 1999) IRES elements from yeast are described in Wei et al., PNAS 98:1531-1536, 2001; Komar et al., EMBO 22:1199-1209, 2003; and Dorokhov et al., PNAS 99:5301-5306, 2002.

In preferred applications of the invention, a response element is operatively linked to one or more nucleic acids that encode LuxA, LuxB, LuxC, LuxD, LuxE and FMN Oxidoreductase proteins. Examples of response elements include estrogen response element (ERE), dioxin response element, and arsenic response element. The examples below describe use of an ERE to generate yeast cells that are responsive to environmental estrogens. These cells contain a nucleic acid encoding human estrogen receptor (hER-$\alpha$) integrated within their genome, and were transformed with a plasmid harboring two EREs coupled to a PGK promoter operatively linked to luxA and luxB nucleic acids. Upon cellular contact with an estrogenic compound (e.g., steroid hormones, estrogenic contaminants, polychlorinated biphenyls (PCBs)), hER-$\alpha$ binds to the compound and to the ERE, inducing transcription of luxA and luxB. Molecular mechanisms of estrogen action are described in Katzenellenbogen et al., J. Steroid Biochem. Mol. Biol. 74:279-285, 2000; and Krishnan et al., Vitam. Horm. 60:123-147, 2000.

Measuring Luminescence

The eukaryotic cells of the invention can be used in combination with a means for measuring luminescence emitted by the cells when in the presence of an analyte (e.g., estrogen and estrogen-like compounds). Typically, the cells react or interact with an analyte of interest producing a luminescent response that can be quantified by an electronic, optical, or mechanical transducer. The cells contain a specific analyte-responsive regulatory element (e.g., a promoter responsive to an analyte) sequence operatively linked to a nucleic acid coding for a reporter enzyme(s). When the target analyte is present, the reporter nucleic acid is expressed to produce the enzyme(s) responsible for the production of the measured signal. In some applications, the cells may be incorporated in a bioluminescent bioreporter integrated circuit (BBIC), a whole-cell integrated chemical sensor. Cells are maintained in close proximity to the integrated circuit of the BBIC. The IC portion of the BBIC detects and quantifies the luminescence and reports this data to (in some cases wirelessly) a central data collection location. The major components of the IC are the integrated photodetectors, the signal processing, and the wireless circuitry. These major components are described in Simpson, M. L. et al. Trends in Biotechnology, 16:332-338, 1998, and Bolton, E. K. et al., Sensors and Actuators B, 85:179-185, 2002. Information comes into the system when the targeted analyte increases or upregulates expression of one or more nucleic acids in the cells. The system measures and reports the magnitude of the upregulation. Electronic integrated circuits and biosensor devices are described in U.S. patent application Ser. Nos. 09/949,015 and 09/910,360, herein incorporated by reference in their entirety. CMOS microluminometers that may be used in the invention are described in Simpson et al., Sens. Actuators B. Chem. 72:134-140, 2001; and Bolton et al., Sens. Actuators B. Chem. 85:179-185, 2002.

In some applications, the cells of the invention are envisioned for use in bioluminescence detectors that may be used outside of the laboratory. Such detectors are made using IC optical transducers that directly interface with cells (e.g., BBICs, Simpson et al., Sens. Actuators B. Chem. 72:134-140, 2001). These BBICs are generally contained within an approximate 5 mm$^2$ area and consist of two main components; photodetectors for capturing the on-chip bioluminescent bioreporter signals and signal processors for managing and storing information derived from bioluminescence. If preferred, remote frequency (RF) transmitters can also be incorporated into the overall IC design for wireless data relay. Since all required elements are completely self-contained within the BBIC, operational capabilities are realized by simply exposing the BBIC to the desired test sample.

In a preferred embodiment of using the eukaryotic cells of the invention with a BBIC, strain BLYES at an $OD_{600}$ of 0.8 is encapsulated in 2 mm diameter alginate beads and loaded into a 10 cm$^3$ flow cell chamber embedded with a 2 mm$^2$ integrated circuit luminometer (Bolton et al., Sens. Actuators B 85:179-185, 2002; Webb et al., Biotech. Bioeng. 54:491-502, 1997). A sample (e.g., wastewater effluent) containing an analyte (e.g., 17$\beta$-estradiol), or a sample suspected of containing an analyte, is infused through the chamber at a suitable rate (e.g., 2 ml/min). A microcontroller with a 16-bit timer/counter input measures the BBIC digital pulse output and serially transmits this data to a remote computer using a commercially available spread-spectrum radio telemetry system (Adcon Telemetry, Boca Raton, Fla.).

Samples to be Analyzed

Within the invention are methods and compositions for detecting the presence of an analyte in a sample. A sample suitable for analysis using compositions and methods of the invention is any sample which can be contacted with eukaryotic cells containing LuxA, LuxB, LuxC, LuxD, and LuxE proteins in a manner such that an analyte present in the sample is able to contact the cells. Such samples include water, soil, gas, and fecal samples. In preferred embodiments, eukaryotic cells of the invention are used with a microchip and a photodetector to detect environmentally relevant concentrations of estrogen, estrogen-like compounds, or compounds having estrogenic activity in a water sample (e.g., wastewater effluent).

Systems for Detecting an Analyte

A system for detecting the presence of an analyte in a sample includes a eukaryotic cell containing nucleic acids encoding LuxA, LuxB, LuxC, LuxD, and LuxE proteins, as well as a means for detecting luminescence from the eukaryotic cell when the cell is in the presence of the analyte. In a preferred system, the nucleic acids are from *Photorhabdus luminescens*, and at least one nucleic acid is operatively linked to at least one regulatory element that is responsive to an analyte (e.g., estrogen response element). In a particularly preferred system, the eukaryotic cell further contains a nucleic acid encoding FMN Oxidoreductase. The nucleic acid encoding FMN Oxidoreductase may be a frp gene from *Vibrio harveyi*. Any means for detecting luminescence may be used (e.g., a photodiode).

The present invention is further illustrated by the following specific examples. The examples are provided for illustration only and are not intended to be construed as limiting the scope or content of the invention in any way.

EXAMPLES

Example 1

Expression of lux Genes in eukaryotes

Materials and Methods

Strains, plasmids, and growth conditions: Strains and plasmids used in this study are listed in Table 1.

TABLE 1

E. coli and S. cerevisiae strains and plasmids

| Strain plasmid | or Description[a] | Reference or source |
|---|---|---|
| *E. coli* | | |
| DH5α | Φ80d/acZΔM15, recA1, endA1, gyrA96, thi-1, hsdR17 ($r_K-$, $m_K+$), supE44, relA1, deoR, Δ(lacZYA-argF)U169 | Promega |
| *S. cerevisiae* | | |
| W303a | MATa, ade2-1, can1-100, his3-11, 15, leu2-3, 112, trpl-1, ura3-1 | (Miller, NAR 26:3577-3583, 1998) |
| Glaxo-Wellcome (hER-lacZ) | MATa, leu2, his3, ERE-lacZ reporter plasmid and human estrogen receptor gene in the chromosome | Routledge and Sumpter Environmental Toxicology and Chemistry 15:241-248, 1996 |
| HER | hER-lacZ without the ERE-lacZ reporter plasmid | |
| INVSc1 | MATa/MATα, his3Δ1/his3Δ1, leu2/leu2, trpl-289/trpl-289, ura3-52/ura3-52 | Invitrogen |
| Plasmids | | |
| pCR TOPO | 2.1 $Ap^r$, $Kn^r$, TA cloning vector | Invitrogen |
| pBEVY-U | Constitutive, URA3 marker, $Ap^r$ | (Miller, NAR 26:3577-3583, 1998) |
| pBEVY-T | Constitutive, TRP1 marker, $Ap^r$ | (Miller, NAR 26:3577-3583, 1998) |
| pBEVY-L | Constitutive, LEU2 marker, $Ap^r$ | (Miller, NAR 26:3577-3583, 1998) |
| pBEVY-GU | Inducible, URA3 marker, $Ap^r$ | (Miller, NAR 26:3577-3583, 1998) |
| pBEVY-GL | Inducible, LEU2 marker, $Ap^r$ | (Miller, NAR 26:3577-3583, 1998) |

Abbreviations:
$Ap^r$, ampicillin resistance;
$Kn^r$, kanamycin resistance

*E. coli* DH5α, used as a host for plasmid construction and maintenance, was grown in Luria-Bertani (LB) broth at 37° C. with or without 100 μg ampicillin/ml depending on the requirement for plasmid maintenance.

YPD liquid medium (1% yeast extract, 2% peptone, 2% glucose) was used for routine growth of plasmid-free *S. cerevisiae* strains. *S. cerevisiae* strains harboring plasmids were grown in synthetic complete (SC) minimal media containing 0.67% yeast nitrogen base (Invitrogen Corp., Carlsbad, Calif.), 0.01% each of adenine, arginine, cysteine, leucine, lysine, threonine, tryptophan, and uracil, and 0.005% each of aspartic acid, histidine, isoleucine, methionine, phenylalanine, proline, serine, tyrosine, and valine.

The pBEVY family of vectors used in this study contained bi-directional promoters which provide for either constitutive or galactose inducible expression of exogenous proteins (Miller et al., Nucleic Acids Research, 26:3577-3583, 1998). The plasmids pBEVY-U, pBEVY-L, and pBEVY-T each contain two constitutive promoters, a glyceraldehyde 3'-phosphate dehydrogenase (GPD) and a fragment of the alcohol dehydrogenase1 (ADH1), which were fused to regulate protein expression in opposite directions in glucose-containing media. In the plasmids pBEVY-GU and pBEVY-GL, a promoter region between GAL1 and GAL10 strongly regulates the expression of proteins in the presence of the Gal4 transcription factor. Plasmids pBEVY-U and pBEVY-GU contain the URA3 selection marker and were selected on uracil deficient media. Plasmids pBEVY-L and pBEVY-GL carry the LEU2 selection marker and were propagated in SC minimal media lacking leucine. The pBEVY-T vector contains the TRP1 selection marker and was maintained on tryptophan-deficient media.

For constitutive expression of proteins from the vectors pBEVY-U, pBEVY-L, and pBEVY-T, 1% glucose was added to the SC minimal media. For inducible expression of proteins from pBEVY-GU and pBEVY-GL, the induction medium contained 2% galactose and 1% raffinose instead of glucose.

Molecular biology techniques: DNA manipulations were performed according to standard protocols. Plasmids were transformed into *E. coli* and *S. cerevisiae* by electroporation using an Electro Cell Manipulator ECM® 600, (BTX Inc., San Diego, Calif.) according to the manufacturers instructions. Plasmid isolation was performed using Wizard mini or midi-prep kits (Promega, San Luis Obispo, Calif.) or the RPM yeast plasmid isolation kit (BIO101 Inc., Carlsbad, Calif.). Restriction and DNA modifying enzymes were obtained from Promega or New England Biolabs (Beverly, Mass.) and used according to the manufacturer's instructions. The polymerase chain reactions (PCRs) were performed in 25 µl volumes using Ready-To-Go PCR beads (Amersham Pharmacia Biotech Inc., Piscataway, N.J.) and the oligonucleotide primers listed in Table 2.

product was electroporated into *E. coli* DH5α and ampicillin resistant colonies selected. Plasmid DNA was subsequently isolated and sequenced to confirm the presence and orientation of the luxA gene.

Two of these plasmids, designated pGUA9 and pUA12, were then used as cloning vectors for insertion of the luxB gene. luxB was PCR-amplified from *P. luminescens* using forward (LuxBF) and reverse (LuxBR) primers designed to introduce the unique restriction sites SmaI-SpeI at the 5' end and KpnI at the 3' end and then ligated downstream of the GAL1 promoter in pGUA9 and the ADH1 promoter in pUA12 to produce the plasmids pGUA9B19 and pUA12B7 (FIG. 1A). DNA sequencing confirmed proper orientation of the inserts. Plasmids pGUA9B19 and pUA12B7 were introduced into *S. cerevisiae* strains W303a, INVSc1, and hER

TABLE 2

Oligonucleotide primers

| Designation | Sequence [a] | |
|---|---|---|
| LuxAF | 5'-GGATCCGCGGCCGCGGACTCTCTATGAAATTTG-3' | (SEQ ID NO:1) |
| LuxAR | 5'-GTCGACCCTTAGCTAATATAATAGC-3' | (SEQ ID NO:2) |
| LuxBF | 5'-CCCGGGACTAGTAAAGAAATGAAATTTGG-3' | (SEQ ID NO:3) |
| LuxBR | 5'-GGTACCAATCTATTAGGTATATTC-3' | (SEQ ID NO:4) |
| LuxCF | 5'-GGATCCGCGGCCGCGGCAAATATGACTAAAAAATTTC-3' | (SEQ ID NO:5) |
| LuxCR | 5'-GTCGACCCTAGGCTATTATGGGACAAATAC-3' | (SEQ ID NO:6) |
| LuxEF | 5'-CCCGGGACTAGTACAGGTATGACTTCATATG-3' | (SEQ ID NO:7) |
| LuxER | 5'-GGTACCAGGATATCAACTATCAAAC-3' | (SEQ ID NO:8) |
| LuxDF | 5'-GTCGACAGTATGGAAAATGAATC-3' | (SEQ ID NO:9) |
| LuxDR | 5'-CTGCAGTAGATTTTAAGACAGAG-3' | (SEQ ID NO:10) |
| IRESF | 5'-CCTAGGCCCAGTTCGATCCTGGGC-3' | (SEQ ID NO:11) |
| IRESR | 5'-GTCGACTATTGTAATAGGTAATTAC-3' | (SEQ ID NO:12) |
| FrpF | 5'-GTCGACATGAACAATACGATTGAAACC-3' | (SEQ ID NO:13) |
| FrpR | 5'-CTGCAGTTAGCGTTTTGCTAGCCCCTT-3' | (SEQ ID NO:14) |

[a]Newly generated restriction sites are shown in boldface type

Oligonucleotides were synthesized with an Oligo 1000 DNA Synthesizer (Beckman Instruments Inc., Fullerton, Calif.). DNA sequencing was performed with the ABI Big Dye Terminator Cycle Sequencing reaction kit on an ABI 3100 DNA Sequencer (Perkin-Elmer Inc., Foster City, Calif.). The initial sequence data text files were edited following comparison with the same data displayed in four-color electropherograms before they were analyzed further.

Cloning of the luxA and luxB genes into the pBEVY-U and pBEVY-GU vectors: The luxA gene was PCR amplified from *P. luminescens* using forward. (LuxAF) and reverse (LuxAR) primers (Table 2) to introduce the restriction sites BamHI-NotI at the 5' end and SalI at the 3' end. The PCR amplified fragment was digested with BamHI and. SalI and cloned into compatible sites within the pBEVY-U and pBEVY-GU vectors downstream of the GPD and GAL10 promoters, respectively (FIG. 1A). Each ligation reaction (Table 1) and transformants selected on SC minimal selective media. Light emission was assayed for in the presence of n-decylaldehyde.

Cloning of the luxC and luxE genes into the pBEVY-T, pBEVY-L, and pBEVY-GL vectors: The luxC and luxE genes were cloned bi-directionally into the pBEVY-T, pBEVY-L and pBEVY-GL vectors (FIG. 1B). PCR amplified fragments of luxC (using primers LuxCF and LuxCR with restriction sites BamHI-NotI-5' and AvrII-SalI-3') were cloned into the BamHI-SalI sites of the pBEVY-T, pBEVY-L, and pBEVY-GL vectors to yield plasmids pTC5, pLC10, and pGLC2, respectively. Insertions were confirmed by DNA sequencing. The luxE gene was then amplified from *P. luminescens* with a LuxEF (SmaI-SpeI-5')/LuxER (KpnI-3') primer set and cloned into the SmaI-KpnI sites of pTC5, pLC10, and pGLC2 under the control of the ADH1 or GAL1 promoters to yield pTCE7, pLCE8, and pGLCE4 (Table 4). Insertions were confirmed by DNA sequencing. Plasmid pTCE7 or pLCE8 were co-transformed with plasmid pUA12B7 into *S. cerevisiae* strain W303a.

Plasmid pLCE8 was co-transformed with pUA12B7 into *S. cerevisiae* strain hER. Transformants containing pUA12B7 and pTCE7 were grown on SC minimal media deficient in uracil and tryptophan, while transformants containing pUA12B7 and pLCE8 were selected on SC minimal media lacking uracil and leucine. Colonies growing on the selection media were screened for light emission in the absence of n-decylaldehyde. Similarly, pGLCE4 and pGUA9B19 were co-transformed into *S. cerevisiae* strains W303a, hER, and INVSc1. Colonies were selected on galactose inducible media and screened for light production without n-decylaldehyde addition.

Cloning luxD into the pTCE7, pLCE8, and pGLCE4 constructs: The luxD gene was cloned into pTCE7, pLCE8, and pGLCE4 downstream of the luxC gene (FIG. 1B). luxD was PCR amplified from *P. luminescens* using the LuxDF and LuxDR primers which were designed to introduce SalI and PstI restriction sites. The resulting product was cloned into the pCR® 2.1-TOPO vector using the TOPO TA Cloning Kit (Invitrogen Corp., Carlsbad, Calif.) to produce the plasmid pTAluxD, which was purified, sequenced, and further used to clone the IRES fragment upstream of the luxD gene. The IRES fragment was PCR amplified from *S. cerevisiae* genomic DNA using the IRESF and IRESR primer pairs containing AvrII and SalI overhangs, cloned into a pCR® 2.1-TOPO vector to yield pTAIRES, and sequenced.

The modified IRES was then removed from the TA vector with a BamHI-SalI double digest, purified, and cloned into pTAluxD previously digested with BamHI and SalI, resulting in the construct designated pTAIRESluxD4. pTAIRESluxD4 was digested with AvrII and PstI to generate an IRES-luxD insert which was gel-purified and cloned into compatible sites within pTCE7, pLCE8, and pGLCE4 downstream of the luxC gene to generate the plasmids pTCIRESDE7, pLCIRESDE8, and pGLCIRESDE4, respectively. Plasmid pLCIRESDE8 was electroporated along with pUA12B7 into *S. cerevisiae* strains W303a and hER. Plasmid pTCIRESDE7 was electroporated with pUA12B7 into *S. cerevisiae* strain W303a. Plasmid pGLCIRESDE4 was cotransformed with pGUA9B19 into *S. cerevisiae* strains W303a, hER, and INVSc1. Transformants were selected on SC minimal media and screened for light emission in the absence of n-decylaldehyde.

Cloning frp into pLCIRESDE8 construct: The frp gene was PCR amplified from *V. harveyi* genome with FrpF and FrpR set of primers introducing AvrII and SalI restriction sites and cloned into pCR 2.1 TOPO vector to yield pTAfrp. A BamH1-Sal1 digest of IRES from pTAIRES was fused into the similar sites of pTAfrp to generate pTAIRESfrp. pTAIRESfrp was further digested with EcoR1 to produce IRESfrp fragment which was cloned into the same site of pLCIRESDE8 downstream of luxE (FIG. 1C). The resulting pLCIRESDEIRESfrp was selected for luminescence studies in the W303a and hER strains of *S. cerevisiae*.

Cell growth and bioluminescence assays: Yeast cells containing either pUA12B7 alone or in combination with pTCE7, pLCE8, pTCIRESDE7, pLCIRESDE8 or pLCIRESDEIRESfrp were grown with shaking (200 rpm) at 30° C. in 200 ml of SC minimal media containing glucose as a carbon source. Aliquots of 20 ml were withdrawn every 6 h for up to 36 h to assay for absorbance at 600 nm ($OD_{600}$) and light emission at 490 nm.

To study the expression of proteins from the GAL1 and GAL10 promoters, yeast cells harboring either pGUA9B 19 alone or in combination with pGLCE4 or pGLCIRESDE4 were propagated in 100 ml of SC minimal media containing 2% raffinose, centrifuged, and inoculated at an $OD_{600}$ of 0.4 into 200 ml of induction media containing 2% galactose and 1% raffinose. Aliquots of 20 ml were then collected every 2 h until the luminescent signal began decaying. All light emission values were obtained with a Deltatox® photoluminometer (Strategic Diagnostics Inc., Newark, Del.) using an integration time of 1 sec. Luminescence from yeast cells containing only pUA12B7 or pGUA9B19 was determined after addition of 25 µl of 1% n-decylaldehyde to a 1 ml subculture.

Luminescence from yeast cells containing either the luxA, B, C, and E genes (pUA12B7 and pTCE7 or pLCE8) or the luxA, B, C, D, and E genes (pUA12B7 and pTCIRESDE7 or pLCIRESDE8 or pLCIRESDEIRESfrp) on constitutive vectors was detected from a 1 ml subculture with or without the addition of n-decylaldehyde. Similarly, luminescence was recorded from yeast cells containing plasmids pGUA9B19 and pGLCE4 or pGLCIRESDE4 after galactose induction with or without n-decylaldehyde addition. Specific bioluminescence was calculated as photons/sec and normalized to growth rate by dividing by $OD_{600}$. *S. cerevisiae* strains transformed with vectors not containing a lux insert were used as controls and treated in parallel with the experiments described above.

Cell lysis, polyacrylamide gel electrophoresis, and Western blotting: Yeast cells from 5 ml, 18 h cultures were lysed in 200 µl of breaking buffer (50 mM sodium phosphate, pH 7.4, 1 mM EDTA, 5% glycerol, 1 mM PMSF) by vortexing with acid washed glass beads (Current Protocols In Molecular Biology, ed. Ausubel et al., Greene Publishing and Wiley-Interscience, New York, 1997). Protein concentrations were determined by the Coomassie Plus protein assay (Pierce, Rockford, Ill.). Twenty micrograms of total protein were applied per lane on 12% SDS polyacrylamide gels and separated.

For Western blot analysis, proteins were transferred to PVDF membranes and the blots reacted with antibodies (1:10000) raised against LuxD-specific peptide (Genemad Synthesis, Inc., South San Francisco, Calif.). Blots were developed with the Bio-Rad goat anti-rabbit IgG AP Immunoblot assay kit (Bio-Rad, Hercules, Calif.).

Results

Cloning and expression of the luxA and luxB genes: To express the luxA and luxB genes simultaneously, two bi-directional vectors were used, pBEVY-U and pBEVY-GU (FIG. 1A). The luxA and luxB genes were cloned into these vectors downstream of the GPD or GAL10 and ADH1 or GAL1 promoters to form plasmids pUA12B7 (constitutive) and pGUA9B19 (galactose inducible). When the construct pUA12B7 was transformed into *S. cerevisiae* strains W303a, hER, and INVSc1, all strains exhibited an increase in specific bioluminescence in the presence of n-decylaldehyde. The luciferase activity of the transformed yeast cells, growing in 1% glucose SC minimal media, was determined after addition of 25 µl of 1% n-decylaldehyde to 1 ml subcultures removed at varying times. Peak bioluminescence occurred after 18 h growth (late logarithmic phase, $OD_{600} \approx 2.2$), with W303a (pUA12B7) yielding the highest light response ($4.23 \pm 0.05 \times 10^6$ photons/sec/$OD_{600}$ as compared to $2.30 \pm 0.03 \times 10^6$ photons/sec/$OD_{600}$ for hER (pUA12B7) and $1.56 \pm 0.04 \times 10^6$ photons/sec/$OD_{600}$ for INVSc1 (pUA12B7)). Bioluminescence decreased beyond 18 h as cultures entered stationary phase. Specific bioluminescence was calculated in triplicate from three independent experiments.

Analysis of variance (ANOVA) calculations (P=0.05) indicated that significant differences in light production among strains occurred at the 12 h time point and thereafter. Significant differences were similarly present among time points at 12 h and beyond. In all cases, the response profile featured an immediate peak in bioluminescence after addition of n-decylaldehyde. A second peak in luminescence could not be induced through the addition of further substrate or shaking to stimulate oxygen saturation. Control strains produced background levels of bioluminescence of less than 100 photons/sec/$OD_{600}$.

To determine luxA and luxB expression under the control of the inducible promoters in pBEVY-GU, colonies transformed with pGUA9B 19 were grown in induction media containing galactose and specific bioluminescence measured with growth (Table 3).

pLCE8 in addition to pUA12B7. Cultures were grown in 1% glucose SC minimal media with continuous shaking at 30° C. for 24 h. At times indicated, 1 ml subcultures were removed and held without shaking for 10 min. Photon counts were then taken in (A) the absence of n-decylaldehyde or (B) with the addition of 25 μl of 1% n-decylaldehyde.

Figure 2:
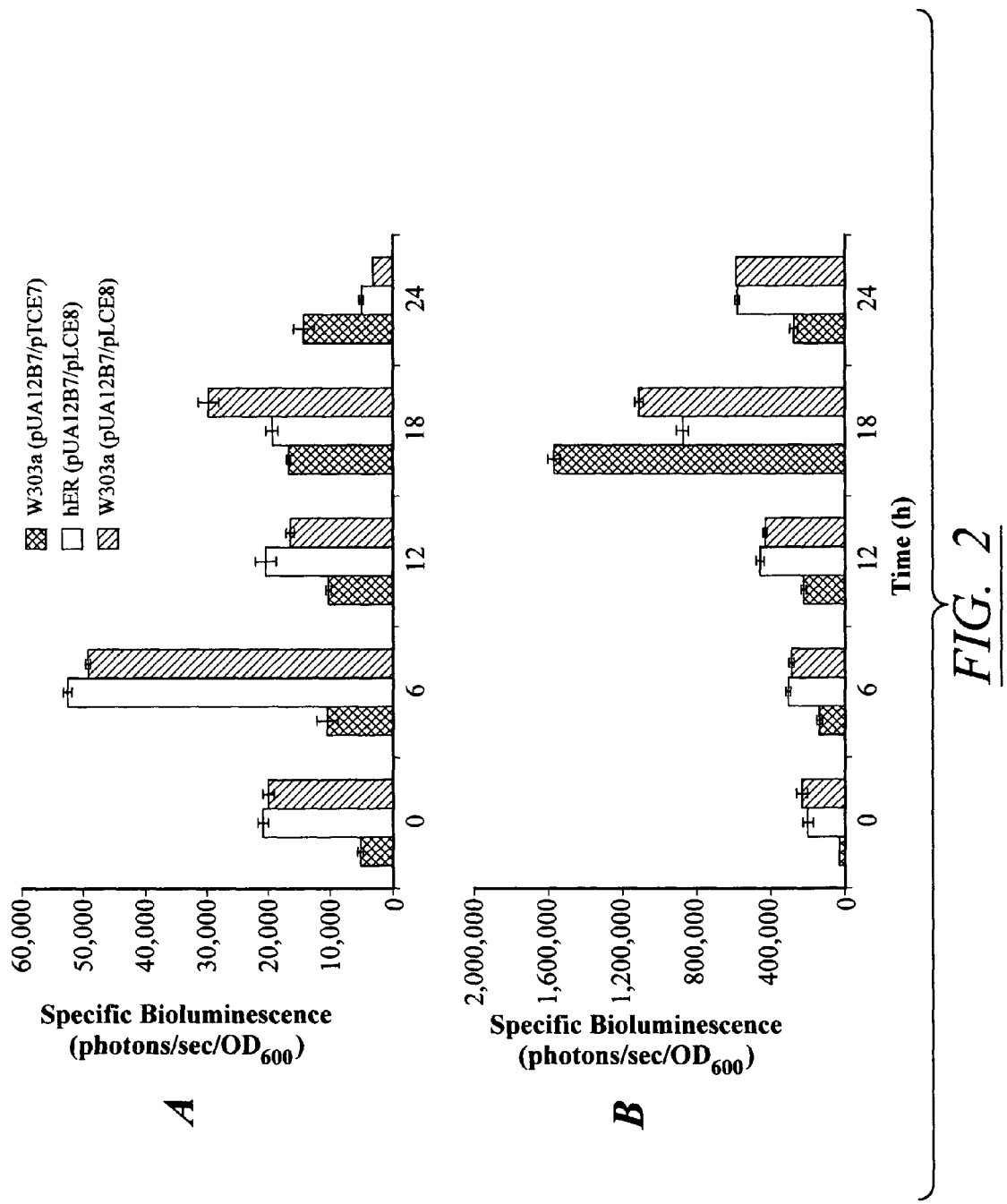
FIG. 2. is a pair of graphs showing simultaneous expression of luxAB and luxCE in *S. cerevisiae* strains W303a and hER. Photon counts were then taken in (A) the absence of n-decylaldehyde or (B) with the addition of 25 μ of 1% n-decylaldehyde.
Figure 3:
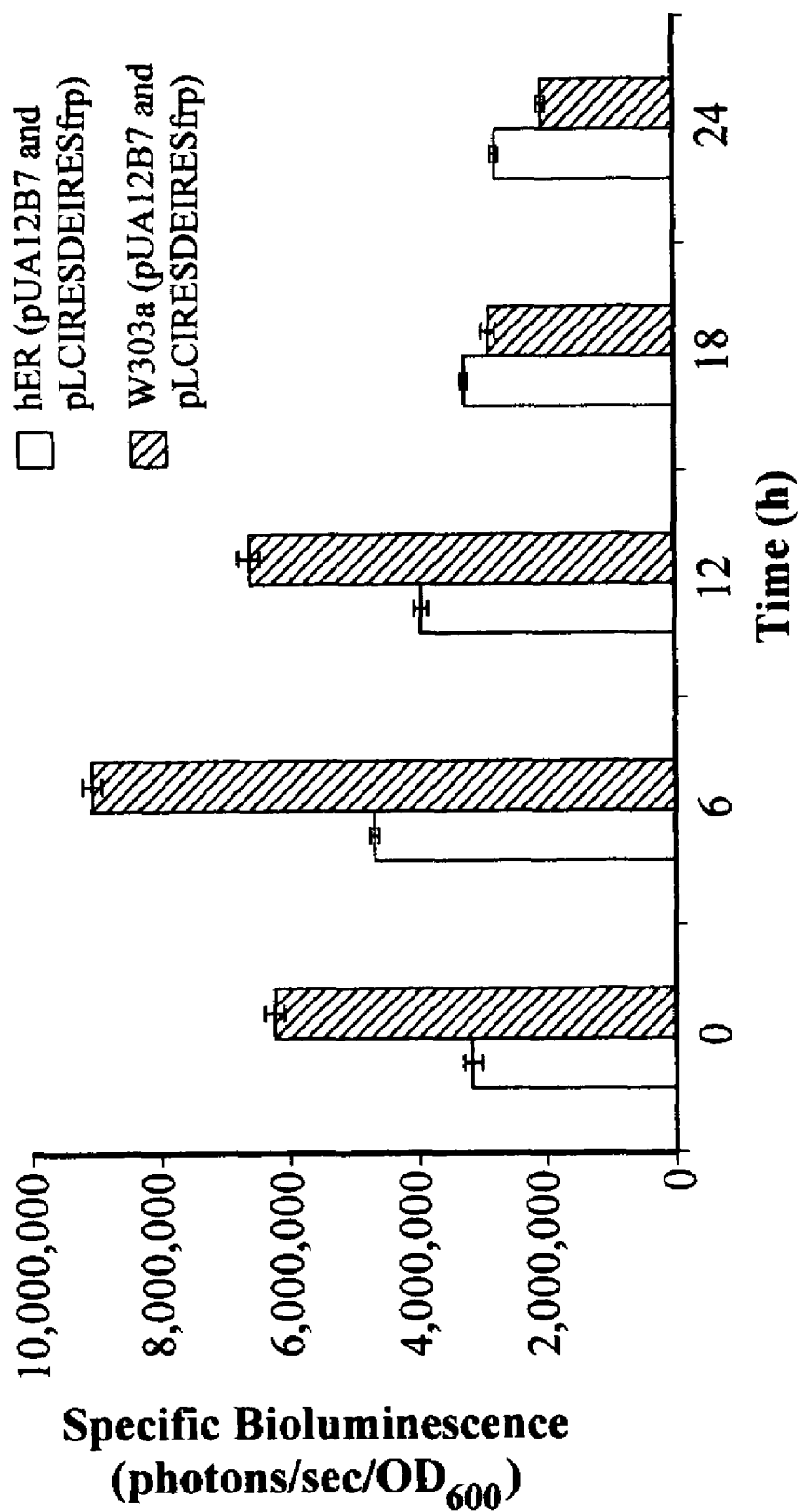
FIG. 3. is a graph showing the difference in bioluminescence between the hER and W303a *S. cerevisiae* strains co-expressing frp gene with samples drawn from continuously shaking cells.

To ascertain whether the low bioluminescent responses were due to inadequate intracellular aldehyde concentrations, experiments were repeated with samples now receiving supplemental n-decylaldehyde. The constitutive constructs generated significantly higher bioluminescent responses (FIG. 2B), but overall values still remained significantly lower than the n-decylaldehyde induced responses in the corresponding constructs containing only the luxA and B genes. n-decylaldehyde addition to the galactose inducible constructs also yielded significantly higher light responses (approximately 10-fold greater than that seen in constructs not exposed to n-decylaldehyde.

TABLE 3

Specific bioluminescence detected from S. cerevisiae strains containing designated lux genes cloned into galactose inducible pBEVY vectors. Bioluminescence was assayed every 2 h after induction. The 8 h timepoints, shown in table, consistently produced the highest bioluminescence levels (n = 9).

| PBEVY constructs | Specific bioluminescence (photons/sec/$OD_{600}$) × $10^5$ | | |
|---|---|---|---|
|  | W303a | hER | INVSc1 |
| PGUA9B19[a] (luxA and B) | 6.08 ± 0.13 | 4.49 ± 0.18 | 4.24 ± 0.30 |
| pGUA9B19/pGLCE4[b] (luxA, B, C, and E) | 0.49 ± 0.01 | 0.14 ± 0.01 | 0.25 ± 0.01 |
| pGUA9B19/pGLCIRESDE 4[b] (luxA, B, C, E, and D) | 4.52 ± 0.14 | 3.87 ± 0.11 | 3.64 ± 0.13 |

[a]Luminescence detected after addition of 25 μl 1% n-decylaldehyde to 1 ml subcultures
[b]Luminescence values without n-decylaldehyde addition Results demonstrated that maximum bioluminescence was consistently produced 8 h after galactose induction, when $OD_{600}$ reached approximately 2.2. Photon emissions decreased beyond 8 h growth. Strain W303a (pGUA9B19) produced the largest bioluminescent response, approximately 1.4-fold higher than that of strains hER (pGUA9B19) and INVSc1 (pGUA9B19).

Light emissions from the inducible pGUA9B19 containing strains were always significantly lower than those seen in the constitutive pUA12B7 containing strains (t test, P=0.05). For example, the highest bioluminescent response produced by strain W303a (pGUA9B19) was approximately 7-fold lower than the highest response seen in strain W303a (pUA12B7).

Cloning and expression of the luxC and luxE genes: The luxC and luxE genes were cloned into pBEVY-T and pBEVY-L vectors downstream of the GPD and ADH1 promoters, respectively, and into pBEVY-GL vectors under the control of the inducible GAL10 and GAL1 promoters, respectively (FIG. 1B). Assuming that S. cerevisiae cells maintain a native pool of myristoyl CoA, bioluminescence without n-decylaldehyde addition was predicted from yeast strains transformed with both the luxAB and luxCE pBEVY constructs. Although this proved to be the case, bioluminescent levels were much lower than expected, only attaining maximum values of approximately 50,000 photons/sec/$OD_{600}$ for both the constitutive (FIG. 2A) and inducible (Table 3) constructs. Specific bioluminescence was determined from yeast cultures containing either pTCE7 or Cloning and expression of the luxD gene: Due to the low levels of bioluminescence produced in the luxAB/luxCE dual transformants assayed above, it was hypothesized that intracellular myristoyl CoA concentrations in S. cerevisiae were too low to adequately drive the luminescent reaction. The luxD gene was therefore cloned and incorporated into the previously constructed pBEVY constructs in front of an IRES fragment to ensure maximal expression (FIG. 1B). The resulting strains, W303a (pUA12B7/pTCIRESDE7), W303a (pUA12B7/pLCIRESDE8), and hER (pUA12B7/pLCIRESDE8) were then assayed for light production in the absence of n-decylaldehyde.

Maximum bioluminescence was again seen 18 h after induction, with strain W303a (pUA12B7/pLCIRESDE8) yielding a bioluminescent response 33-fold greater than that of its corresponding luxD deficient strain (W303a (pUA12B7/pLCE8)). Luminescence was detected from a 1 ml subculture of yeast recombinants harboring pUA12B7 and either pLCIRESDE8 or pTCIRESDE7 without the addition of n-decylaldehyde. Subcultures were held without shaking for 10 min prior to obtaining photon counts. Similarly, strain hER (pUA12B7/pLCIRESDE8) produced a bioluminescent response 24-fold greater than its luxD deficient equivalent hER (pUA12B7/pLCE8). Bioluminescence from the W303a (pUA12B7/pTCIRESDE7) strain was extremely poor, seemingly indicating that the TRP1 selection marker was not optimal in these yeast constructs. Western blots were used to confirm luxD expression.

Bioluminescent expression from the galactose inducible constructs (W303a and hER harboring pGUA9B 19/pGLCIRESDE4) was significantly lower (>3-fold) than their constitutive counterparts (Table 3). Responses typically averaged 400,000 photons/sec/$OD_{600}$ and were comparable to the luxAB-only constructs (pGUA9B 19) that had been induced with n-decylaldehyde (Table 3).

The low values of luminescence from pGLCIRESDE4 and pGUA9B19 constructs were observed in hER and INVSc1 as compared to W303a. During expression studies of luxAB and luxCDE genes in yeast, a maximal baseline of specific bioluminescence (250,000 photons/sec/$OD_{600}$) was noted in all samples during 18 h of growth on continuous shaking. The luminescence from the samples enhanced to a maximal value, when photons were recorded after the samples were kept still without shaking for 10 min followed by a pulse shaking. The luminescence from these samples started decaying immediately after a high light intensity peak, which could be further resumed after 10 min of still incubation. Moreover, further addition of the aldehyde substrate to these cultures did not help in enhancing the luminescence values.

These results indicate that the expression of luxC, D, and E genes was enough to produce aldehyde substrate that was fully utilized by the luciferase protein in the bioluminescence reaction.

Cloning and expression of flavin oxidoreductase from frp gene: The yeast cells expressing the complete cassette of luxCDABE operon did not generate very high levels of luminescence continuously during shaking. To overcome the problem of luminescence decay from bioluminescent cells, frp gene encoding for NADPH dependent FMN oxidoreductase was cloned and co-expressed with lux genes (FIG. 1C). The simultaneous expression of frp gene in W303a and hER strains not only stabilized but also enhanced the luminescence to 3.5-5.5 fold as compared to the strains without frp gene.

Figure 6:
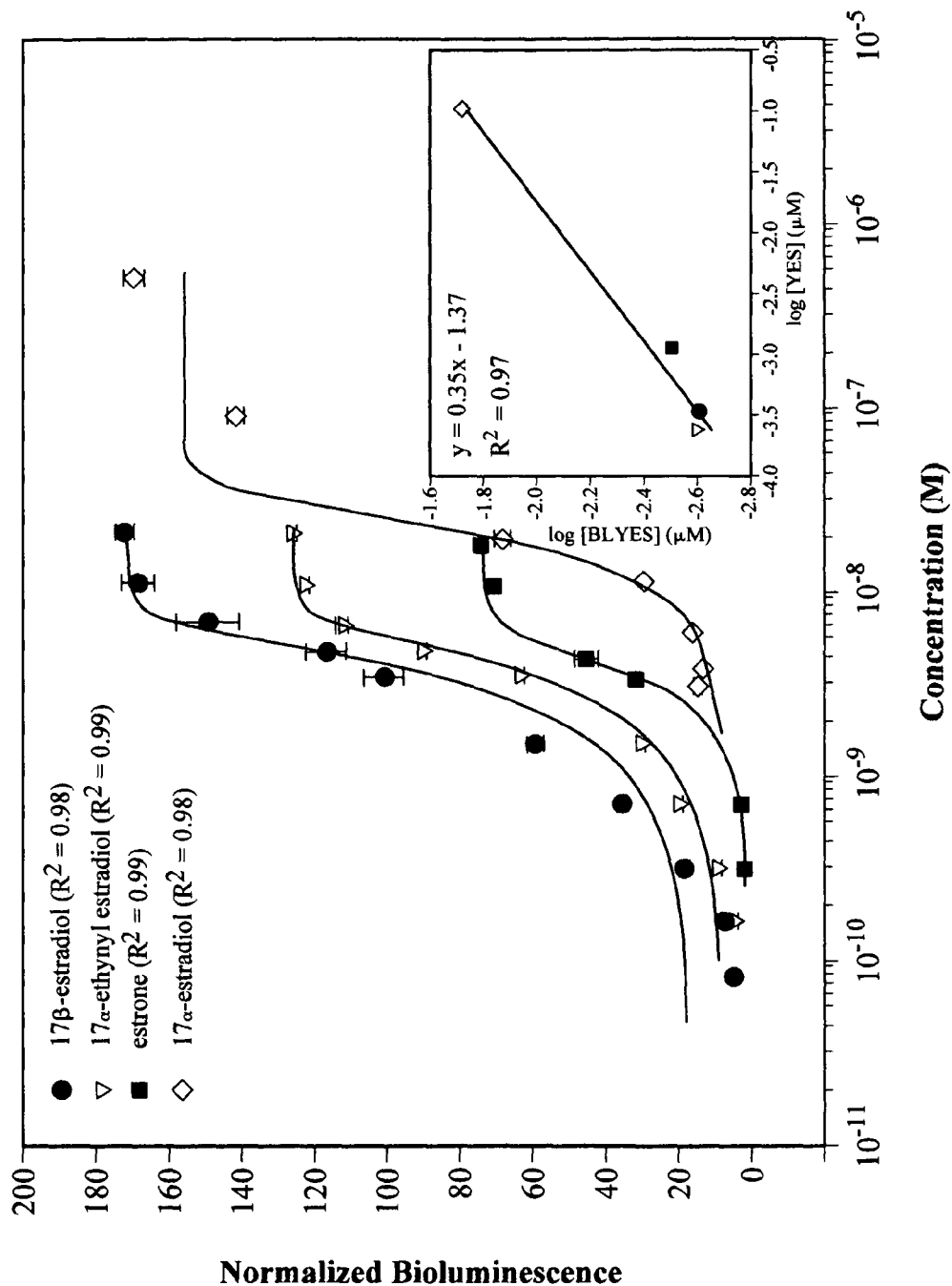
FIG. 6 is a graph showing $EC_{50}$ dose response profiles of the S. cerevisiae BLYES bioreporter to the estrogenic compounds 17β-estradiol (●), 17α-ethynyl estradiol (▽), estrone (■), and 17α-estradiol (◇); (n=4). Inset: $EC_{50}$ dose response correlations between the lacZ based YES and lux based BLYES estrogenic assays.

The maximum specific bioluminescence was observed from the samples withdrawn from continuously shaking cultures after 6 h of growth for both W303a ($9.0\pm0.27\times10^6$ photons/sec/OD) and hER ($4.6\pm0.08\times10^6$ photons/sec/OD) strains (FIG. 6). Though the photons/sec kept increasing with increase in OD of the cultures, specific bioluminescence started decreasing after 6 h of growth in all the samples. The levels of bioluminescence from hER strain remained 1.95 fold lower as compared to W303a strain. Moreover, no improvement in luminescence levels was observed when samples were tested for luminescence after 10 min of incubation without shaking.

Table 4 shows constructs prepared and used as described above.

TABLE 4

| pUA12 | pBEVY-U harboring luxA |
|---|---|
| pUA12B7 | pBEVY-U harboring luxA and luxB |
| PGUA9 | pBEVY-GU harboring luxA |
| PGUA9B19 | pBEVY-GU harboring luxA and luxB |
| pTC5 | pBEVY-T harboring luxC |
| pLC10 | pBEVY-L harboring luxC |
| PGLC2 | nBEVY-GL harboring luxC |
| PTCE7 | pBEVY-T harboring luxC and luxE |
| PLCE8 | pBEVY-L harboring luxC and luxE |
| pGLCE4 | pBEVY-GL harboring luxC and luxE |
| pTAIRES | PCR2.1 TOPO vector harboring IRES |
| pTAluxD | PCR2.1 TOPO vector harboring luxD |
| pTAIRESluxD4 | PCR2.1 TOPO vector harboring IRES fragment and luxD |
| pTCIRESDE7 | pBEVY-T harboring luxC, luxD and luxE |

TABLE 4-continued

| pLCIRESDE8 | pBEVY-L harboring luxC, luxD and luxE |
|---|---|
| pGLCIRESDE4 | pBEVY-GL harboring luxC, luxD and luxE |
| PTAfrp | PCR2.1 TOPO vector harboring frp |
| pTAIRESfrp | PCR2.1 TOPO vector harboring IRES fragment and frp |
| pLCIRESDEIRESfrp | PLCIRESDE8 harboring frp |

[a]Abbreviations:
$Ap^r$, ampicillin resistance;
$Kn^r$, kanamycin resistance

The luxA gene was inserted in the BamHI-SalI sites of the pBEVY-GU and pBEVY-U vectors to generate pGUA9 and pUA12. The luxB gene was cloned in the SmaI-KpnI sites of pGUA9 and pUA12 downstream of the GAL1 and ADH1 promoters to produce the inducible plasmid pGUA9B19 and the constitutive plasmid pUA12B7 (FIG. 1A).

The luxC gene, containing AvrII and SalI restriction sites at its 3' end, was cloned into the BamHI-SalI sites of pBEVY-GL, pBEVY-T and pBEVY-L downstream of the GAL10 and GPD promoters to produce pGLC2, pTC5, and pLC10, respectively. The luxE gene was inserted in the SmaI-KpnI sites of these constructs downstream of either the GAL1 or ADH1 promoter. The luxD gene was finally cloned downstream of the luxC gene in the AvrII-PstI sites and placed under the control of an IRES amplified from *S. cerevisiae* (FIG. 1C) The resulting plasmid constructs were designated pGLCIRESDE4, pTCIRESDE7, and pLCIRESDE8. Arrows indicate direction of transcription or translation of promoters and IRES inserts. Relevant restriction sites are indicated as follows: A, AvrII; B, BamHI; E, EcoRI; K, KpnI; N, NotI; P, PstI; Sc, SacI; S1, SalI; Sm, SmaI; Sp, SpeI; X, XmaI (FIG. 1B).

Example 2

Expression of lux Genes in *S. cerevisiae* and On-line Microchip Biosensing of Environmental Estrogens Experimental Protocol Strain construction: Strain BLYEV was transformed with the plasmids pUA12B7 and pLCDEfrp. Both plasmids were constructed on a pBEVY vector platform containing a constitutive leftward glyceraldehyde 3'-phosphate dehydrogenase (GPD) promoter and rightward alcohol dehydrogenase1 (ADH1) promoter (Miller et al., Nuc. Acids Res. 26:3577-3583, 1998). The luxA gene was inserted in the BamHI-SalI sites of pBEVY-U downstream of the GPD promoter while the luxB gene was cloned in the SmaI-KpnI sites downstream of the ADH1 promoter to produce the constitutive plasmid pUA12B7 (FIG. 1). For plasmid pLCDEfrp, the luxC gene, containing AvrII and SalI restriction sites at its 3' end, was cloned into the BamHI-SalI sites of pBEVY-L downstream of the GPD promoter. The luxE gene was inserted in the SmaI-KpnI sites downstream of the ADH1 promoter. The luxD gene was cloned downstream of the luxC gene in the AvrII-PstI sites and placed under the control of an IRES amplified from *S. cerevisiae*. Another IRES fragment was fused to the frp gene derived from *V. harveyi* and ligated into a unique EcoRI site downstream of luxE (FIG. 1). Both plasmids were then transformed into *S. cerevisiae* strain W303a growing in synthetic complete (SC) media as previously described, with glucose added at 1% (v:v) to initiate expression (Routledge, E. J. & Sumpter, J. P., Environ. Toxicol. Chem. 15:241-248, 1996).

Figure 5:
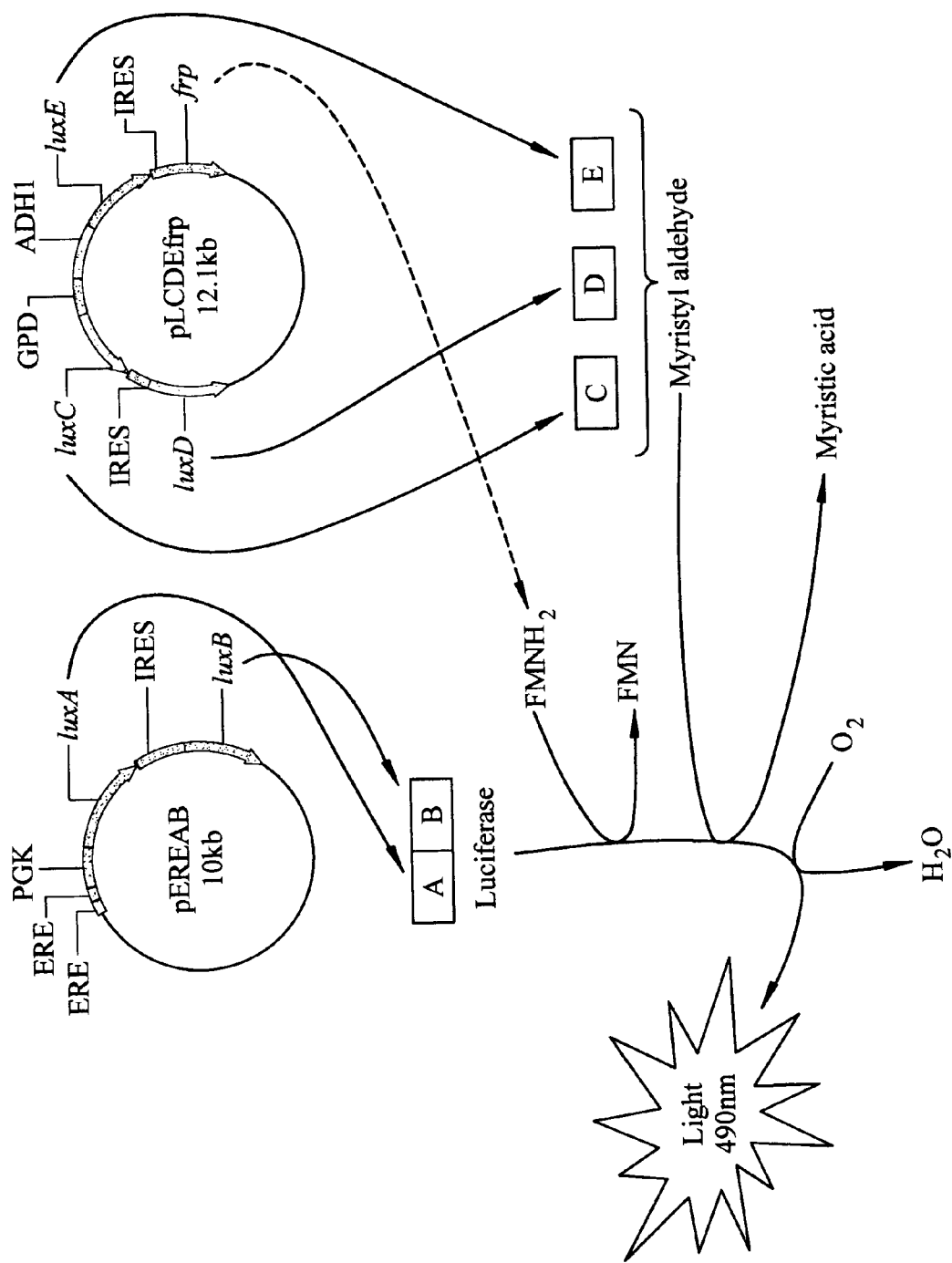
FIG. 5 is a schematic illustration of construction of the estrogen inducible bioreporter S. cerevisiae BLYES. Synthesis of luxA is regulated on plasmid pEREAB by. upstream incorporation of two sequential estrogen response elements (ERE) coupled to a phosphoglycerate kinase (PGK) promoter. The luxB component of the luciferase is supplied via independent expression from a fused IRES. hER-α is inserted chromosomally. See FIG. 1 and text for description of plasmid pLCDEfrp.

The estrogen reporter strain BLYES was constructed directly on the YES expression plasmid backbone (Routledge, E. J. & Sumpter, J. P., Environ. Toxicol. Chem. 15:241-248, 1996) via excision of the lacZ reporter gene and insertion of a luxA/IRES/luxB clonal fragment synthesized with compatible restriction site termini (FIG. 5). The human estrogen receptor hER-α was integrated chromosomally. The yeast strain was then cotransformed with plasmid pLCDEfrp.

Cell growth and bioluminescence assays: Yeast cells were grown with shaking (200 rpm) at 30° C. in SC minimal media containing 1% (v:v) glucose. Aliquots (20 ml) were withdrawn every 2 h to measure absorbance ($OD_{600}$) and light emission at 490 nm using a Deltatox photoluminometer (Strategic Diagnostics, Newark, Del.) at an integration time of 1 sec. Bioluminescence was normalized to growth rate by dividing by $OD_{600}$. n-decylaldehyde (Sigma, 99%), when required, was added at 0.025%. S. cerevisiae strains transformed with vectors not containing lux inserts were used as controls and treated in parallel with the experiments described above.

Estrogen induction assays: Strain BLYES was grown in SC media overnight at 30° C. and then concentrated via centrifugation to an approximate $OD_{600}$ of 0.15 in 20 ml

TABLE 5

Response times and maximum bioluminescence achieved with each successive lux component insertion

| Genetic components | Response time (h) | Maximum bioluminescence (photons/sec/OD) |
|---|---|---|
| luxAB + n-decylaldehyde | NA | 4.2 (± 0.06) × $10^6$ |
| luxAB + luxCE | 6 | 4.9 (± 0.05) × $10^4$ |

SC media. Two hundred microliters were transferred to each well of black 96-well Microfluor microtiter plates (Dynex Technologies, Chantilly, Va.) with addition of estrogenic compounds within indicated molar ranges. Bioluminescence was measured every 10 min in a Perkin-Elmer Victor (Meighen, E. A., Microbiol. Rev. 55:123-142, 1991), Multilabel Counter at an integrattion time of 1 sec/well, concurrent with absorbance ($OD_{600}$) readings. Bioluminescence was normalized to growth rate by dividing by $OD_{600}$.

| luxAB + luxCDE | 6 | 1.6 (±0.07) × $10^6$ |
| luxAB + luxCDE + frp | <1 | 1.9 (±0.03) × $10^6$ |

NA - not applicable, response occurs immediately after addition of n-decylaldehyde For the BBIC experiments, strain BLYES at an $OD_{600}$ of 0.8 was encapsulated in 2 mm diameter alginate beads and loaded into a 10 $cm^3$ flow cell chamber embedded with a 2 $mm^2$ integrated circuit luminometer (Bolton et al., Sens. Actuators B 85:179-185, 2002 and Webb et al., Biotech. Bioeng. 54:491-502, 1997). Wastewater effluent artificially contaminated with 17β-estradiol at 8 ppb was infused through the chamber at a rate of 2 ml/min. A microcontroller with a 16-bit timer/counter input measured the BBIC digital pulse output and serially transmitted this data to a remote computer using a commercially available spread-spectrum radio telemetry system (Adcon Telemetry, Boca Raton, Fla.).

Results and Discussion

Bioluminescence expression from S. cerevisiae bioreporter BLYEV: The establishment of lux-based bioluminescent phenotypes in yeast and other eukaryotes has so far been relegated solely to luxAB derivatives (Almashanu et al., J. Biolumin. Chemilumin, 5:89-97, 1990 and Olsson et al., Gene, 81:335-347, 1989). The omission of the luxC, luxD, and luxE genes excludes synthesis of the aldehyde substrate, which therefore must be added exogenously, usually in the form of n-decylaldehyde, to initiate bioluminescence. Unfortunately, n-decylaldehyde is toxic to lower eukaryotes, making luxAB yeast bioreporters unsuitable for in vivo analyses (Hollis et al., FEBS Lett. 506:140-142, 2001). In higher eukaryotes, however, luxAB reporter gene constructs can functionally produce bioluminescence in the presence of n-decylaldehyde but at a considerably reduced activity. In these constructs, the bacterial bicistronic luxAB gene is fused into a eukaryotic-compatible monocistronic transcriptional unit. Experimental evidence indicates that this fusion impedes proper folding of the resulting LuxAB luciferase, in part due to drastically reduced heat lability at optimal growth temperatures (Escher et al., Proc. Natl. Acad. Sci. U.S.A., 86:6528-6532, 1989). Our genetic manipulations therefore adopted a different approach, wherein the luxA and luxB genes were cotranscribed independently from separate constitutive promoters and allowed to freely interact, assemble, and fold in the cytosolic matrix. This was accomplished through bi-directional expression of the luxA and luxB genes in a pBEVY vector containing constitutive leftward (glyceraldehyde 3'-phosphate (GPD)) and rightward (alcohol dehydrogenasel (ADH1)) promoters (Miller et al., Nuc. Acids Res., 26:3577-3583, 1998). The resulting plasmid, designated pUA12B7, when cloned independently into S. cerevisiae, was able to generate n-decylaldehyde dependent bioluminescence at levels approaching 4.2 (±0.06)×$10^6$ photons/sec, representing a 20-fold increase over that reported for constitutive expression from fused luciferases (Table 5) (Kirchner et al., Gene, 81:349-354, 1989).

Figure 4:
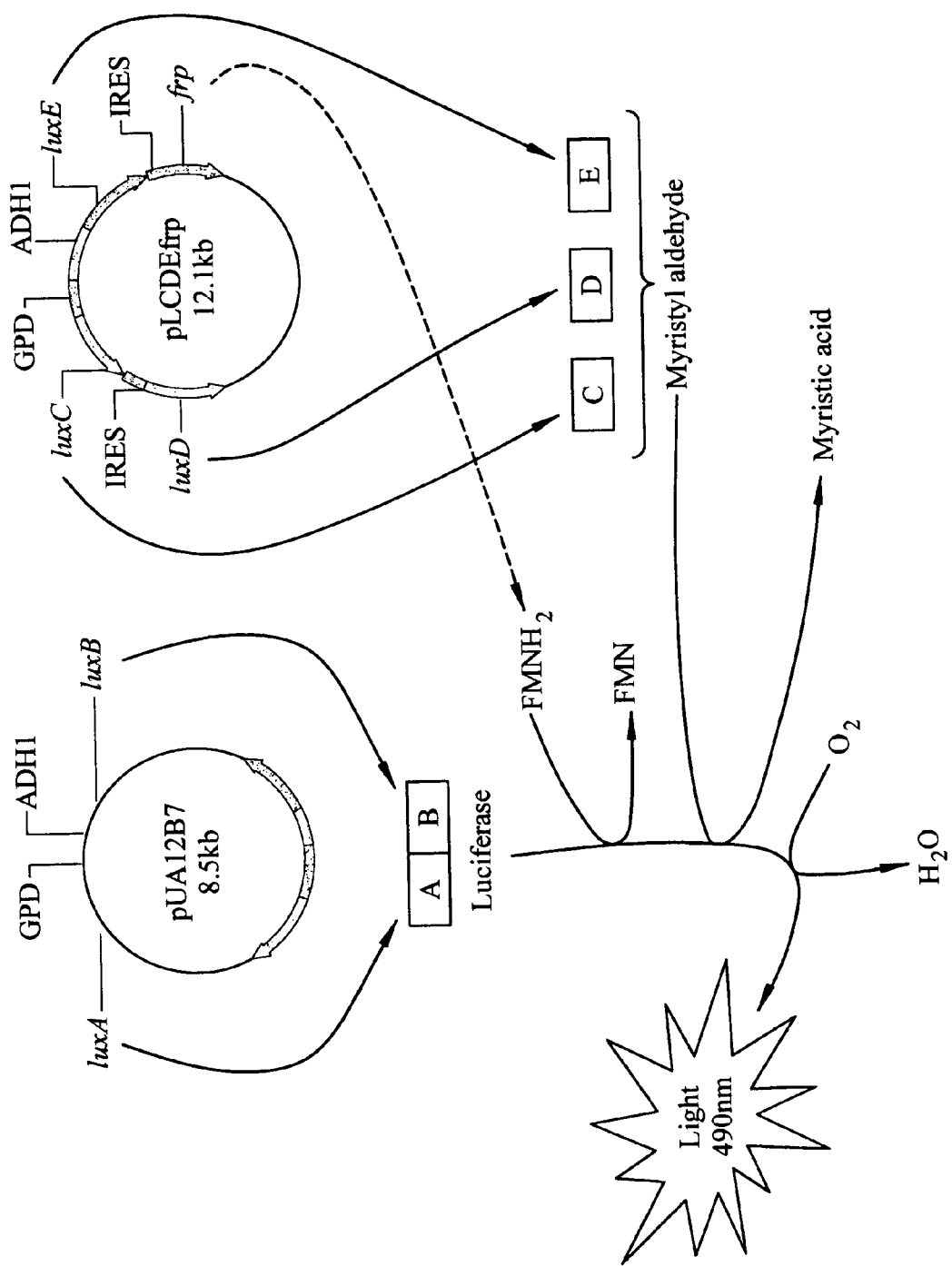
FIG. 4 is a schematic illustration of a method of constructing the bioreporter *S. cerevisiae* BLYEV. The luxA and luxB genes within plasmid pUA12B7 are cotranscribed independently from the glucose inducible, constitutive promoters GPD and ADH1, respectively, to yield the LuxAB luciferase enzyme. The remaining lux cistronic components (luxC, D, and E), as well as an NADPH dependent FMN oxidoreductase gene (frp) are contained within plasmid pLCDEfrp, respectively providing the aldehyde and $FMNH_2$ substrates metabolized during the light emitting reaction. Incorporation of IRES fragments ensures independent expression of luxD and frp. With glucose added to the growth medium as an inducing substrate, strain BLYEV is capable of fully autonomous expression of bioluminescence in less than 1 h.

The second phase of this research effort required insertion of the luxC, luxD, and luxE genes into S. cerevisiae for establishment of n-decylaldehyde independent bioluminescent expression. An initial construct included only the luxC and luxE genes cloned into a pBEVY vector in similar fashion to luxA and luxB (FIG. 1). When inserted into S. cerevisiae in tandem with the pUA12B7 luxAB plasmid, however, bioluminescent levels approached only 4.9 (±0.05)×$10^4$ photons/sec (Table 1). Supplemental addition of n-decylaldehyde increased bioluminescence >10-fold, proving that the aldehyde substrate was limiting. The luxD gene was therefore necessary.

luxD was cloned into the previously constructed pBEVY luxCE construct downstream of a yeast internal ribosomal entry site (IRES) (FIG. 4). IRES elements allow ribosomes to bind directly at an AUG start codon rather than requiring initial recognition at the 5' cap site and subsequent scanning for the start site (Hellen, C. U. T. & Sarnow, P., Genes Dev., 15:1593-1612, 2001.) If the AUG start site is located within the open reading frame, translation can be initiated internally and the monocistronic mRNA essentially becomes multiply-cistronic. Therefore, it was hypothesized that the insertion of an IRES fragment between the luxC and luxD genes would catalyze bicistronic synthesis of LuxC and LuxD. Western blots confirmed that LuxD was indeed being monomerically expressed from the luxCDE plasmid and bioluminescence from S. cerevisiae containing the luxAB and luxCDE plasmids was produced at levels 33 times greater than in cells absent of luxD (Table 1). However, the bioluminescent response was transient, usually sustaining itself for less than 30 sec. We knew that the yeast bioreporter was being supplied with adequate amounts of two of the substrates required for the luminescent reaction, oxygen and the fatty aldehyde. This left us with the final substrate, $FMNH_2$, as the only remaining limiting factor.

The $FMNH_2$ pool in yeast cells is likely generated from the flavin reductase activity of chorismate synthase (Henstrand et al., Mol. Microbiol., 22:859-866, 1996), which is probably not active enough to produce adequate amounts of $FMNH_2$ for optimal bioluminescence from the available luciferase. To supplement $FMNH_2$ concentrations, the frp gene, encoding the NADPH dependent FMN oxidoreductase from *Vibrio harveyi*, was cloned into the luxCDE plasmid to form the final plasmid construct pLCDEfrp (FIG. 4). An IRES site was again used to ensure independent expression. Insertion of pLCDEfrp and pUA12B7 into *S. cerevisiae* generated the strain designated as BLYEV. Bioluminescence from strain BLYEV was 5.5-fold greater than that in a similar construct void of the frp gene. As well, bioluminescence generally persisted for up to 20 h, initiating in less than 1 h and becoming maximal after approximately 8 h ($1.9\pm0.03\times10^6$ photons/sec) (Table 1). Bioluminescence subsequently decreased after 8 h due to cell death, as determined by a corresponding decrease in optical density. When in vivo bioluminescence intensity was directly compared with a prokaryotic luxCDABE bioreporter using CCD imaging, strain BLYEV generated nearly twice the photonic output. Strain BLYEV emitted a maximum of 1900 photons/sec/$\mu m^2$ as compared to 1100 photons/sec/$\mu m^2$ emitted by *E. coli* pUTK2.

Bioluminescent sensing of endocrine disruptors: The environmental deposition of natural, pharmaceutical, and synthetic chemicals with estrogenic activity is thought to be associated with numerous human and wildlife physiological disorders, prompting the development of various assays to screen for estrogenic potencies (Baker, V. A., Toxicology in Vitro, 15:413-419, 2001). As a model towards demonstrating the applicability and inherent advantages of self-bioluminescent yeast bioreporters, we converted strain BLYEV into an environmental estrogen detector and functionally compared it to the established yeast estrogen screen (YES) (Routledge, E. J. & Sumpter, J. P., Environ. Toxicol. Chem., 15:241-248, 1996). The yeast cells in the YES assay contain the human estrogen receptor (hER-$\alpha$) and a plasmid based estrogen response element (ERE)/lacZ reporter fusion. Activation of the estrogen receptor induces synthesis of the lacZ-encoded $\beta$-galactosidase which interacts with an exogenously added substrate to produce a red coloring of the assay medium. Although proven effective for the in vitro determination of estrogenic activity, the YES assay's incubation time of 2-4 days is impractical when considering the thousands of chemicals requiring screening.

Using a genetic scheme similar to that for YES cells, *S. cerevisiae* was transformed with plasmid pEREAB, which harbors two sequential EREs coupled to a phosphoglycerate kinase (PGK) promoter inserted upstream of luxA. The luxB luciferase component was independently supplied from an internally fused IRES. hER-$\alpha$ was chromosomally based, and plasmid pLCDEfrp supplied the remaining components for the light emitting reaction. The resulting estrogen reporter was designated as *S. cerevisiae* BLYES (FIG. 5). Strain BLYES was exposed to the estrogenic compounds 17$\beta$-estradiol, 17$\alpha$-estradiol, 17$\alpha$-ethynyl estradiol, estrone, and 3,4',5-trichloro-4-biphenylol and compared to the YES assay. The $EC_{50}$ dose response profiles and comparative correlations are shown in FIG. 4. With an $R^2$ of 0.97, the assays compared relatively well. Sensitivities of both assays decreased in the order 17$\beta$-estradiol>17$\alpha$-ethynyl estradiol>estrone>17$\alpha$-estradiol, with no significant response generated from 3,4',5-trichloro-4-biphenylol. The BLYES assay yielded an average response time of 2-4 h as opposed to 2-4 days for the YES assay. However, this shortened response time results in a 5 to 10-fold lower detection limit than that of the YES assay. This was not unexpected since the extended incubation period of the YES assay permits increased sensitivity due to the serial accumulation of $\beta$-galactosidase over time. The BLYES assay, however, is rate limited by the substrate pools immediately available.

Figure 7:
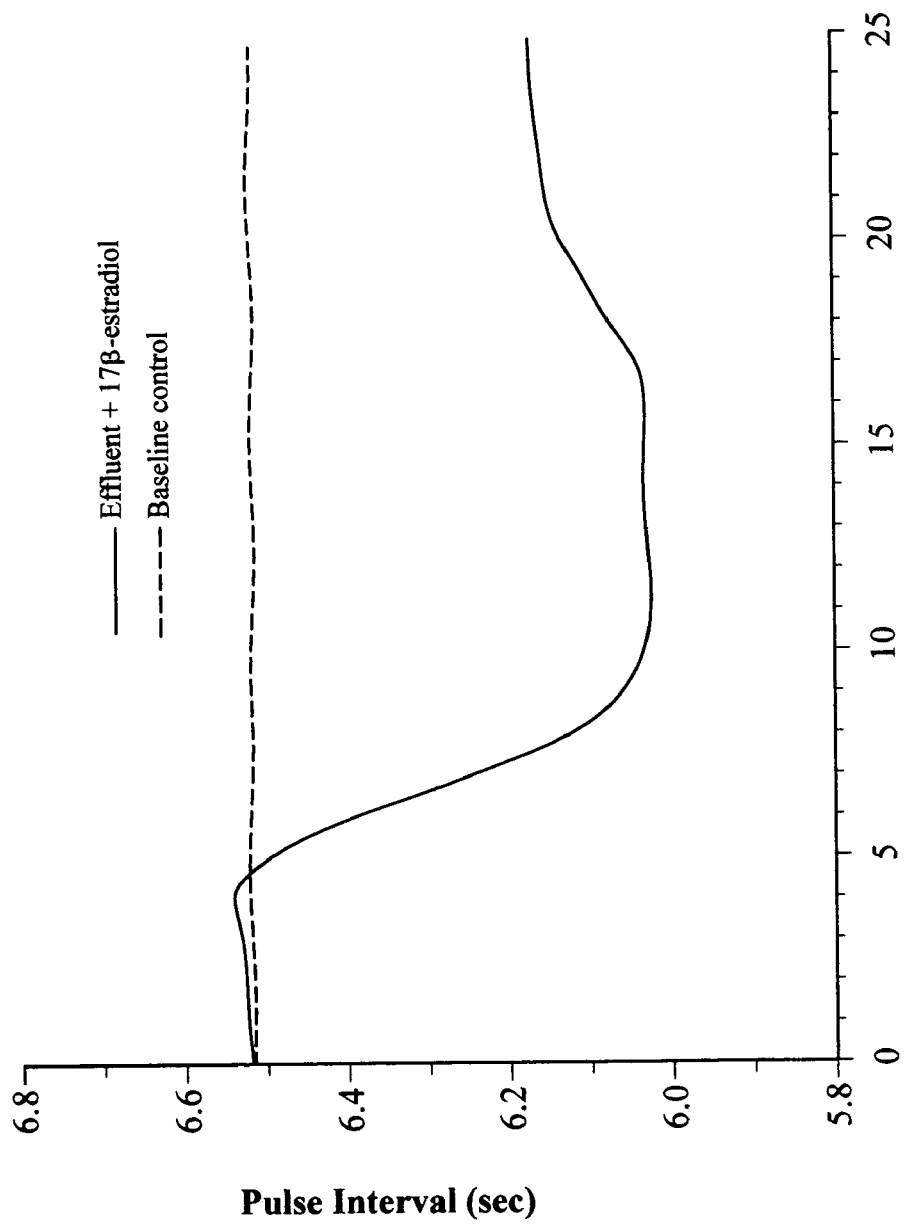
FIG. 7 is a plot of a bioluminescence profile established with the remote BBIC detection system.

On-line microchip detection of 17$\beta$-estradiol in wastewater effluent: The effectiveness of strain BLYES towards on-line monitoring of endocrine disruptors was demonstrated using a microchip embedded flow cell infused with 17$\beta$-estradiol contaminated wastewater effluent. The microchip, termed a bioluminescent bioreporter integrated circuit (BBIC), provides a sensitive measure of bioluminescence by integrating the photoinduced current of an on-board n-well/p-substrate photodiode and converting this measurement to a digital pulse interval in seconds that is inversely proportional to the amount of collected light (Simpson et al., Trends Biotech., 16:332-338, 1998). The solid line in FIG. 7 depicts results obtained after flow-cell exposure of alginate encapsulated BLYES cells to wastewater effluent artificially contaminated with 17$\beta$-estradiol at 8 ppb. The dashed line denotes the baseline output of cells exposed to unadulterated wastewater effluent. Significant differences between baseline and experimental bioluminescence occurred after 4.8 h (t test, $\alpha=0.05$). Alginate encapsulated *S. cerevisiae* BLYES bioreporters exposed to wastewater devoid of 17$\beta$-estradiol produced pulse intervals averaging 6.5 sec (dashed line). Bioluminescence induction from BLYES encapsulated cells in response to flow through wastewater effluent artificially contaminated with 17$\beta$-estradiol at 8 ppb (solid line) produced a pulse interval response that significantly differed from the baseline within 4.8 h of addition and maximizing at approximately 6.0 sec (the pulse interval is inversely proportional to measured bioluminescence) (n=2).

Example 3

Glow-in-the-dark Beer™

Brewer's yeast including Lux A, B, C, D, E can be used to make ethanol-contained beverages made by fermentation (e.g., beer). The yeast is added to a liquid containing a carbohydrate source (e.g., sugar) to create a mixture. The mixture is placed under conditions that allow yeast-mediated fermentation to proceed (e.g., about room temperature) resulting in the generation of carbon dioxide and ethanol in the liquid mixture. The ethanol-containing beverage thus made should be maintained under conditions that allow the yeast to live and bioluminesce.

OTHER EMBODIMENTS

This description has been by way of example of how the compositions and methods of the invention can be made and carried out. Various details may be modified in arriving at the other detailed embodiments, and many of these embodiments will come within the scope of the invention. Therefore, to apprise the public of the scope of the invention and the embodiments covered by the invention, the following claims are made.

What is claimed is:

1. A eukaryotic cell induced to express LuxA, LuxB, LuxC, LuxD, LuxE, and $FMNH_2$ in sufficient quantities to render the cell stably luminescent under conditions where exogenously added aldehyde is absent, wherein the eukaryotic cell is selected from the group consisting of a mammalian cell and a yeast cell.

2. The eukaryotic cell of claim 1, wherein the cell comprises a nucleic acid encoding LuxA, a nucleic acid encoding LuxB, a nucleic acid encoding LuxC, a nucleic acid encoding LuxD, and a nucleic acid encoding LuxE.

3. The eukaryotic cell of claim 1, further comprising a nucleic acid encoding FMN oxidoreductase.

4. The eukaryotic cell of claim 2, wherein at least one of the nucleic acids is operatively linked to at least one regulatory element.

5. The eukaryotic cell of claim 4, wherein the at least one regulatory element is responsive to an analyte.

6. The eukaryotic cell of claim 4, wherein the at least one regulatory element is operatively linked to a promoter sequence.

7. The eukaryotic cell of claim 4, wherein the regulatory element comprises an IRES.

8. The eukaryotic cell of claim 7, wherein the IRES is a eukaryotic IRES.

9. The eukaryotic cell of claim 8, wherein the eukaryotic IRES is a yeast IRES.

10. The eukaryotic cell of claim 9, wherein the yeast IRES is from *Saccharomyces cerevisiae*.

11. The eukaryotic cell of claim 4, wherein the regulatory element comprises a promoter sequence.

12. The eukaryotic cell of claim 11, wherein the promoter sequence is an inducible promoter sequence.

13. The eukaryotic cell of claim 11, wherein the promoter sequence is a constitutive promoter sequence.

14. A yeast cell induced to express LuxA, LuxB, LuxC, LuxD, LuxE, and $FMNH_2$ in sufficient quantities to render the cell stably luminescent under conditions where exogenously added aldehyde is absent.

15. The cell of claim 14, wherein the yeast cell is a *Saccharomyces cerevisiae* cell.

16. The cell of claim 14, wherein the yeast cell is a *Candida albicans* cell.

17. The eukaryotic cell of claim 1, wherein the cell is contained on or within a solid substrate.

18. The eukaryotic cell of claim 17, wherein the solid substrate is a microchip.

19. The eukaryotic cell of claim 2, wherein the nucleic acids are capable of being expressed in the eukaryotic cell.

* * * * *

SEQUENCE LISTING

<160> NUMBER OF SEQ ID NOS: 14

<210> SEQ ID NO 1
<211> LENGTH: 33
<212> TYPE: DNA
<213> ORGANISM: Photorhabdus luminescens

<400> SEQUENCE: 1
ggatccgcgg ccgcggactc tctatgaaat ttg           33

<210> SEQ ID NO 2
<211> LENGTH: 25
<212> TYPE: DNA
<213> ORGANISM: Photorhabdus luminescens

<400> SEQUENCE: 2
gtcgaccctt agctaatata atagc                     25

<210> SEQ ID NO 3
<211> LENGTH: 29
<212> TYPE: DNA
<213> ORGANISM: Photorhabdus luminescens

<400> SEQUENCE: 3
cccgggacta gtaaagaaat gaaatttgg                 29

<210> SEQ ID NO 4
<211> LENGTH: 24
<212> TYPE: DNA
<213> ORGANISM: Photorhabdus luminescens

<400> SEQUENCE: 4
ggtaccaatc tattaggtat attc                      24

<210> SEQ ID NO 5
<211> LENGTH: 38
<212> TYPE: DNA
<213> ORGANISM: Photorhabdus luminescens

<400> SEQUENCE: 5
ggatccgcgg ccgcggcaaa tatgactaaa aaaatttc       38

<210> SEQ ID NO 6
<211> LENGTH: 30
<212> TYPE: DNA
<213> ORGANISM: Photorhabdus luminescens

<400> SEQUENCE: 6
gtcgacccta ggctattatg ggacaaatac                30

<210> SEQ ID NO 7
<211> LENGTH: 31
<212> TYPE: DNA
<213> ORGANISM: Photorhabdus luminescens

<400> SEQUENCE: 7
cccgggacta gtacaggtat gacttcatat g              31

<210> SEQ ID NO 8
<211> LENGTH: 25
<212> TYPE: DNA
<213> ORGANISM: Photorhabdus luminescens

```
<400> SEQUENCE: 8
ggtaccagga tatcaactat caaac                                      25

<210> SEQ ID NO 9
<211> LENGTH: 23
<212> TYPE: DNA
<213> ORGANISM: Photorhabdus luminescens

<400> SEQUENCE: 9
gtcgacagta tggaaaatga atc                                        23

<210> SEQ ID NO 10
<211> LENGTH: 23
<212> TYPE: DNA
<213> ORGANISM: Photorhabdus luminescens

<400> SEQUENCE: 10
ctgcagtaga ttttaagaca gag                                        23

<210> SEQ ID NO 11
<211> LENGTH: 24
<212> TYPE: DNA
<213> ORGANISM: Saccharomyces cerevisiae

<400> SEQUENCE: 11
cctaggccca gttcgatcct gggc                                       24

<210> SEQ ID NO 12
<211> LENGTH: 25
<212> TYPE: DNA
<213> ORGANISM: Saccharomyces cerevisiae

<400> SEQUENCE: 12
gtcgactatt gtaataggta attac                                      25

<210> SEQ ID NO 13
<211> LENGTH: 27
<212> TYPE: DNA
<213> ORGANISM: Vibrio harveyi

<400> SEQUENCE: 13
gtcgacatga acaatacgat tgaaacc                                    27

<210> SEQ ID NO 14
<211> LENGTH: 27
<212> TYPE: DNA
<213> ORGANISM: Vibrio harveyi

<400> SEQUENCE: 14
ctgcagttag cgttttgcta gcccctt                                    27
```